United States Patent
Gardner et al.

(12)

(10) Patent No.: US 6,737,269 B2
(45) Date of Patent: May 18, 2004

(54) MULTI-STATE GENETIC OSCILLATOR

(75) Inventors: Timothy Gardner, Jamaica Plain, MA (US); James J. Collins, Newton Center, MA (US)

(73) Assignee: Boston University, Boston, MA (US)

( * ) Notice: Subject to any disclaimer, the term of this patent is extended or adjusted under 35 U.S.C. 154(b) by 24 days.

(21) Appl. No.: 09/872,338

(22) Filed: Jun. 1, 2001

(65) Prior Publication Data

US 2002/0061528 A1 May 23, 2002

Related U.S. Application Data

(63) Continuation-in-part of application No. PCT/US99/28592, filed on Dec. 1, 1999.
(60) Provisional application No. 60/110,616, filed on Dec. 2, 1998.

(51) Int. Cl.[7] .................. C12N 15/09; C12N 15/00; C12N 15/86; C12Q 1/68; C07H 21/04
(52) U.S. Cl. ............. 435/325; 435/235.1; 435/320.1; 435/69.1; 435/6; 435/440; 435/455; 435/471; 536/23.1; 536/24.1
(58) Field of Search .............. 435/6, 320.1, 252.3, 435/325, 440, 455, 471, 69.1, 235.1; 536/23.1, 24.1

(56) References Cited

U.S. PATENT DOCUMENTS

| | | | |
|---|---|---|---|
| 4,833,080 A | 5/1989 | Brent et al. | |
| 5,416,008 A | 5/1995 | Bailey et al. | |
| 5,589,392 A | 12/1996 | Short | |
| 5,814,618 A | 9/1998 | Bujard et al. | 514/44 |
| 5,972,650 A | 10/1999 | Yao | |
| 5,989,910 A | 11/1999 | Mermod et al. | |

FOREIGN PATENT DOCUMENTS

| | | |
|---|---|---|
| DE | 0 136 907 A2 | 10/1984 |
| WO | WO 99/57290 | 11/1999 |
| WO | WO 00/32748 | 6/2000 |
| WO | WO 00/65080 | 11/2000 |

OTHER PUBLICATIONS

Amann et al., Vectors Bearing a Hybrid trp–lac Promoter Useful for Regulated Expression of Cloned Genes in *Escherichia coli*. (1983). *Gene* 25: 167–178.

Amann et al., 'ATG Vectors' for Regulated High–Level Expression of Cloned Genes in *Escherichia coli*. (1985). *Gene* 40: 183–190.

Backman et al., Maximizing Gene Expression on a Plasmid Using Recombination in Vitro. (1978). *Cell* 13: 65–71.

Bailey et al., Molecular Genetics and Control Systems: Biochemical Engineering Fundamentals. Second Edition. Chapter 6: 307–372.

(List continued on next page.)

*Primary Examiner*—Gerry Leffers
(74) *Attorney, Agent, or Firm*—Choate, Hall & Stewart

(57) ABSTRACT

Provided are methods and compositions for regulating gene expression in a cell. The invention provides recombinant multi-state genetic oscillators containing an adjustable-threshold genetic switch that is periodically activated by an oscillating amount of an activator agent. The activating agent is a gene product expressed from a promoter regulated by the adjustable-threshold switch and thus forms a feedback loop that causes periodic switching of the adjustable-threshold switch between an "on" state and an "off" state. Multi-state genetic oscillators are useful to express one or more genes of interest in a periodic manner without requiring a periodic application of an external activating agent.

13 Claims, 14 Drawing Sheets

OTHER PUBLICATIONS

Chen et al., Molecular Design of Expression Systems: Comparison of Different Repressor Control Configurations Using Molecular Mechanism Models. (1991). *Biotechnology and Bioengineering* 38: 679–687.

Chen et al., Construction and characterization of a novel cross–regulation system for regulating cloned gene expression in *Escherichia coli*. (1993) *Gene* 130: 15–22.

Chen et al., Process Characterization of a novel cross–regulation system for cloned protein production in *Escherichia coli*. (1995). *Biotechno. Prog.* 11(4): 397–402.

Cohen, Total Control: Now you can keep bugs in line with genetic clocks and switches. (2000). *New Scientist*.

Crowl et al., Versatile expression vectors for high–level synthesis of cloned gene products in *Escherichia coli*. (1985) *Gene* 38: 31–38.

Dedhia et al., Design of expression systems for metabolic engineering: coordinated synthesis and degradation of glycogen. (1997). *Biotechnol & Bioeng.* 55(2): 420–426.

Gardner et al., Construction of a genetic toggle switch in *Escherichia coli*. (2000). *Nature*. 403: 339–342.

Gardner et al., Neutralizing noise in gene networks. (2000). *Nature* 405: 520–521.

Gardner, Design and Construction of Synthetic Gene Regulatory Networks. (2000). *Ph.D. Dissertation, Boston University*.

Goeddel et al., Expression in *Escherichia coli* of Chemically Synthesized Genes for Human Insulin. (1979) *Proc. Natl. Acad. Sci. USA*, 76 (1): 106–110.

Gorman et al., Regulation of the Yeast Metallothionein Gene. (1986). *Gene*, 48: 13–22.

Hadcock et al., Cross–regulation between G–protein–mediated Pathways, Stimulation of Adenylyl Cyclase Increases Expression of the Inhibitory G–protein $G_{m2}$. (1990). *The Journal of Biological Chemistry* 265 (25): 14784–14790.

Hadcock et al., Cross–regulation between G–protein–mediated Pathways. Activation of the Inhibitory Pathway of Adenylylcyclase Increases the Expression of $\beta_2$ Adrenergic Receptors. (1991). *The Journal of Biological Chemistry* 266 (18): 11915–11922.

Hasty et al., Noise–based switches and amplifiers for gene expression. (2000). *Proc. Natl. Acad. Sci. USA*. 97(5): 2075–80.

Kaufman. High Level Production of Proteins in Mammalian Cells. (1987). *Genetic Engineering: Principles and Methods* 9: 155–198.

Kramer et al., Isolation of Yeast Genes with mRNA levels controlled by phosphate concentration. (1980). *Proc. Natl. Acad. Sci. USA*. vol. 77 (11): 6541–6545.

Lee et al., Genetically Structured Models for lac Promoter–Operator Function in the Chromosome and in Multicopy Plasmids: lac Promoter Function. (1984) *Biotechnology and Bioengineering* XXVI: 1383–1389.

Lee et al., Genetically Structured Models for lac Promoter–Operator Function in the *Escherichia coli* Chromosome and in Multicopy Plasmids: lac Operator Function. (1984). *Biotechnology and Bioengineering* XXVI: 1372–1382.

Monod et al., General Conclusions: Teleonomic Mechanisms in Cellular Metabolism, Growth, and Differentiation. (1961). *Cold Spring Harbor Symposia on Quantitative Biology* XXVI: 389–401.

Moser et al., Characterization and Complementation of pMBI Copy Number Mutant: Effect of RNA 1 Gene Dosage on Plasmid Copy Number and Incompatibility. (1983). *Journal of Bacteriology* 154 (2): 809–818.

Oshima, Regulatory Circuits for Gene Expression: The Metabolism of Galactose and Phosphate. (1982). *The Molecular Biology of the Yeast Saccharomyces: Metabolism and Gene Expression*: 159–180.

PCT International Search Report from PCT/US99/28592.

Platt, Regulation of Gene Expression in the Tryptophan Operon of *Escherichia coli*. (1975). *The Operon*: 263–302.

Ptashne, Repressor and Its Action. (1971). *The Bacteriophage Lambda* 11: 221–237.

Seo et al., Effects of Recombinant Plasmid Content on Growth Properties and Cloned Gene Product Formation in *Escherichia coli*. (1985). *Biotechnology and Bioengineering* XXVII: 1668–1674.

Shockett et al., Diverse strategies for tetracycline–regulated inducible gene expression. (1996). *Proc. Natl. Acad. Sci. USA*. 93: 5173–5176.

Sledziewski et al., Construction of Temperature–Regulated Yeast Promoters Using the MATα2 Repression System. (1988). *Biotechnology* 6: 411–416.

Windass et al., The construction of a synthetic *Escherichia coli trp* promoter and its use in the expression of a synthetic interferon gene. (1982). *Nucleic Acids Research* . 10 (21): 6639–6657.

Cormack, B.P., et al., "*Facs–Optimized Mutants of the Green Fluorescent Protein (GFP)*" Gene, Elsevier Biomedical Press., Amsterdam, NL, vol. 173, 1996, pp. 33–38.

Gardner, Timothy, et al: "*A Theory for Controlling Cell Cycle Dynamics using a Reversibly Binding Inhibitor.*" Proceedings of the National Academy of Sciences of the United States, vol. 95, No. 24, Nov. 24, 1998 (1998–11–24), pp. 14190–14195.

Ishiura Masahiro, et al., "*Expression of a Gene Cluster kai ABC as a Circadian Feedback Process in Cyanobacteria*", Science Washington, D.C., vol. 281, No. 5382, pp. 1519–1523.

Lutz, R., et al., "*Independent and Tight Regulation of Transcriptional Units In Escherichia Coli Via the LACR/O, The TETR/O and ARAC/L1–L2 Regulatory Elements*", Nucleic Acids Research, Oxford University Press, Surry, GB, vol. 6, No. 25, 1997, pp. 1203–1210.

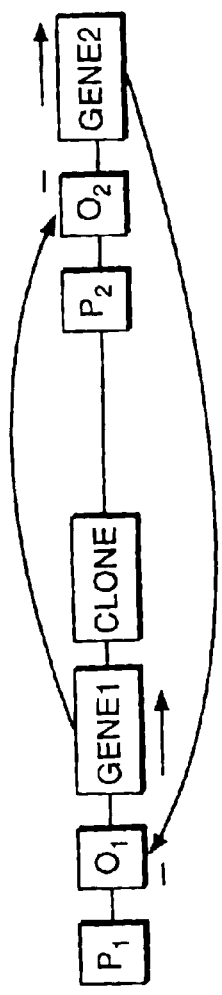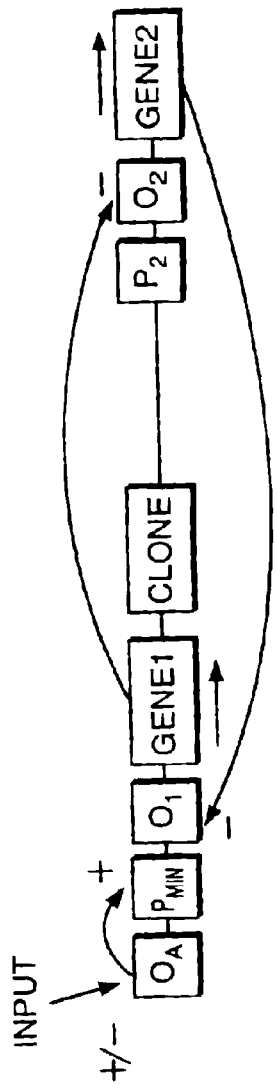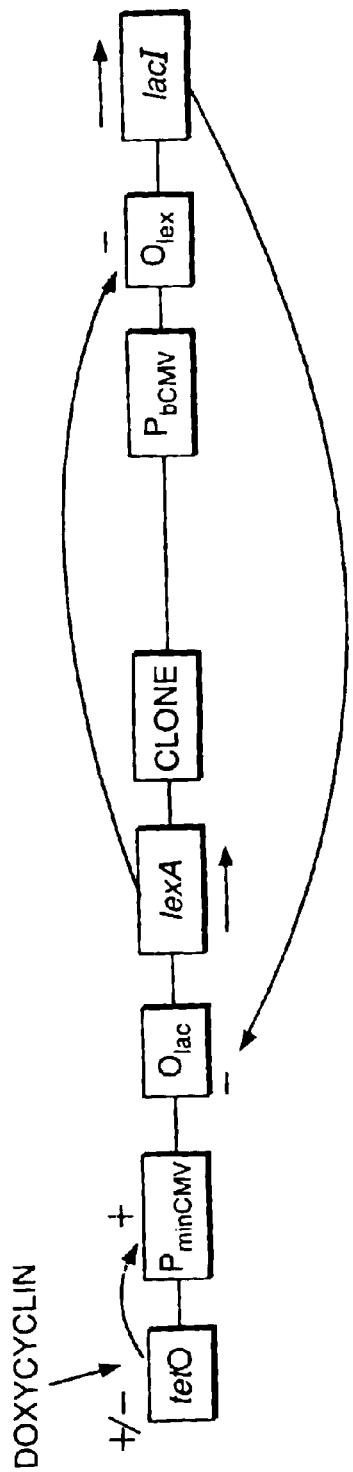

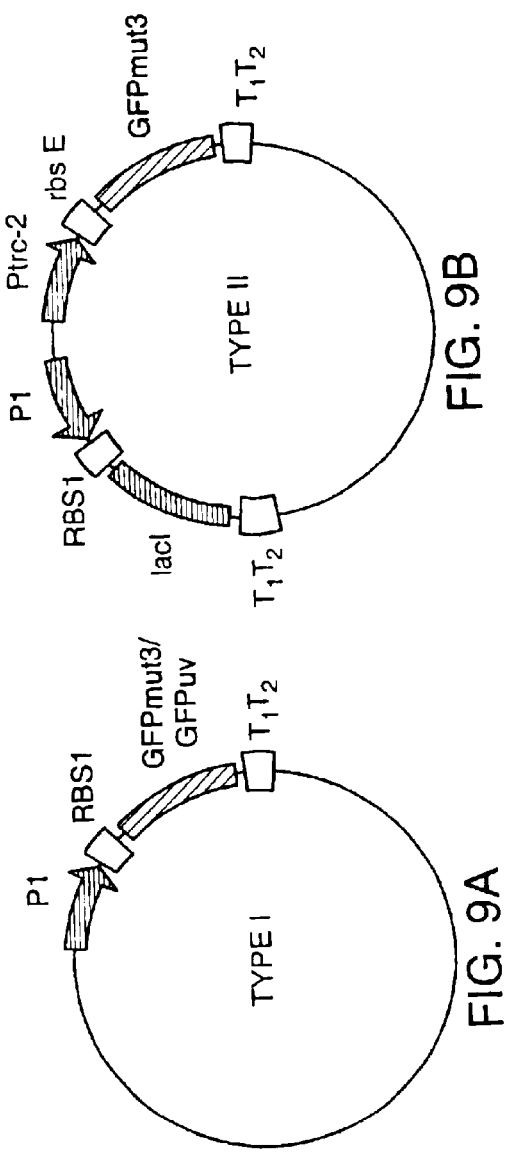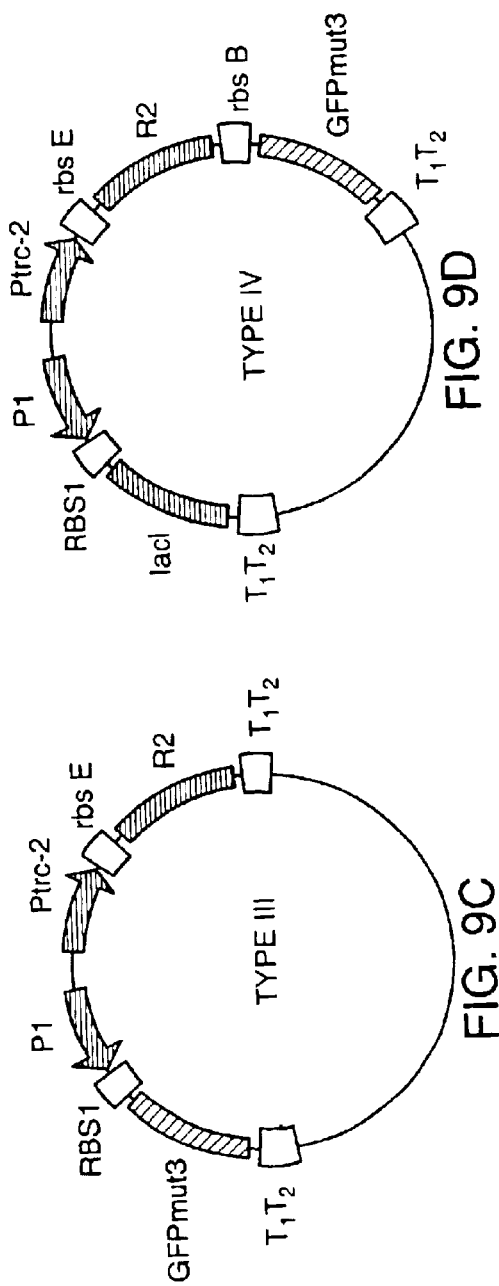
FIG. 9A  FIG. 9B  FIG. 9C  FIG. 9D

| | | |
|---|---|---|
| A | AGGAGGAAAAAAATG | (SEQ ID NO: 4) |
| B | AGGAATTTAAATG | (SEQ ID NO: 5) |
| C | AGGAAACAGACCATG | (SEQ ID NO: 6) |
| D | AGGAAACCGGTTCGATG | (SEQ ID NO: 7) |
| E | AGGAAACCGGTTATG | (SEQ ID NO: 8) |
| F | AGGACGGTTCGATG | (SEQ ID NO: 9) |
| G | AGGAAAGGCCTCGATG | (SEQ ID NO: 10) |
| H | AGGACGGCCGGATG | (SEQ ID NO: 11) |

FIG. 10B

```
gcgtcacacactttgctatgccatagcatttttatccataagattagcggatcctacctgacgctttttatcgca
cgcagtgtgaaacgatacggtatcgtaaaaataggtattctaatcgcctaggatggactgcgaaaaatagcgt
```
I1/I2 — PBAD

```
actctctactgttctccatagatctaatgtgtggaattgtgagcggataacaatttcacacaggaaacccggt   (SEQ ID NO: 12)
tgagagatgacaaagaggtatctagattaccacacccttaacactcgcctattgttaaagtgtgtcctttggcca
```
Olac — SD — From Ptrc

FIG. 12B

MULTI-STATE GENETIC OSCILLATOR

RELATED APPLICATIONS

This application claims priority to, and the benefit of PCT/US99/28592, filed on Dec. 1, 1999, which claims priority to, and the benefit of U.S. Ser. No. 60/110,616, filed on Dec. 2, 1998, the disclosures of which are incorporated by reference herein. Related applications include: U.S. Ser. No. 09/872,868, filed Jun. 1, 2001; and U.S. Ser. No. 09/872,339, filed Jun. 1, 2001, the disclosures of which are incorporated by reference herein.

FIELD OF THE INVENTION

The present invention relates to methods and compositions for regulating gene expression in a cell. In particular, the invention provides multi-state genetic oscillator constructs in which expression of a gene of interest changes periodically in the absence of extraneous agents.

BACKGROUND OF THE INVENTION

Many areas of biotechnology involve regulating the expression of one or more genes of interest by applying an external agent. Typical approaches for regulating gene expression involve natural or engineered transcription factors that activate or inhibit expression of a specific gene in response to a chemical agent [Gossen and Bujard, Proc. Natl. Acad. Sci. USA, 89:5547, 1992; Rivera, et al., Nat. Med., 2:1028, 1996; Yao and Evans, Proc. Natl. Acad. Sci. USA, 93:3346, 1996; Wang, et al., Proc. Natl. Acad. Sci. USA, 91:8180, 1994]. Transcription factors often are introduced into a cell using DNA constructs that express a transcription factor and a gene of interest. Stable activation or inhibition of a transcription factor typically requires that a chemical agent or other stimulus be applied. However, when an oscillating level of expression is desired, it is often problematic to repeatedly apply and remove a stimulus in order to obtain the oscillation. Therefore, there is an ongoing need in the art for self-contained methods and compositions that permit oscillating levels of gene expression in the absence of an external stimulus.

SUMMARY OF THE INVENTION

The invention provides a recombinant multi-state genetic oscillator that can transition the expression of one or more genes of interest from stable "on" to stable "off" states or vice versa in a regular and periodic manner. According to the invention, the expression of one or more genes in the multi-state oscillator are changed from a first expression state to a second expression state by the presence of a preselected amount i.e., an amount of an activating agent equal to or greater than a specific concentration (threshold concentration). When the concentration of the activating agent drops below the threshold concentration, the oscillator returns back to its first expression state. An important feature of the invention is that the concentration of the activating agent is controlled by the expression of one or more regulatory genes in the oscillator switch. The expression of these genes, in turn, is regulated by the state of the multi-state oscillator. Thus a feedback loop is created which causes the oscillator to transition repeatedly and continuously between its two expression states. These repeated transitions produce a periodic change in concentration of the activating agent, the expression of the regulatory gene or genes, and the expression of the gene or genes of interest.

The multi-state oscillator of the invention is characterized as having two alternative expression states. In a first state, a first, inducible, promoter is substantially inactive and a second, constitutive, promoter is active. In a second state, the inducible promoter is active and the constitutive promoter is substantially inactive. Therefore, in the first state, genes that are transcribed from the constitutive promoter are expressed, and in the second state, genes that are transcribed from the inducible promoter are expressed. According to the invention, the activating agent causes a transition from the first expression state to the second expression state when it reaches a preselected or threshold concentration. Once the concentration of activating agent drops below this level, the switch returns back to the first expression state. An important feature of the invention is that the cyclical nature of the switching is controlled by periodic increases and decreases in the concentration of the activating agent. Furthermore, the periodic changes in the concentration of the activating agent are controlled by one or more regulatory genes in the oscillator. The expression of these regulatory genes, in turn, is controlled by the expression state of the oscillator. Thus a feedback loop is created which causes the oscillator to transition periodically between its expression states. By adjusting the rates and/or levels of expression of the activating agent, it is possible to produce an oscillator switch that has a desired periodicity, i.e., the oscillator cycles between its two different expression states and the switch is in one of its different expression states for a desired period of time. Preferably, the transition from the first expression state to the second expression state does not occur in the absence of the threshold concentration of the activating agent. More preferably, the transition from the second expression state to the first expression state does not occur in the presence of a concentration of activating agent equal to or greater than the threshold concentration.

With reference to FIG. 1, the components of a multi-state oscillator of the invention include a first regulatory gene ($R_1$) that is expressed from a first, inducible promoter ($P_1$), and a second regulatory gene ($R_2$) that is expressed from a second, constitutive promoter ($P_2$). A product of the first regulatory gene inhibits or reduces expression of the second regulatory gene, and a product of the second regulatory gene inhibits or reduces expression of the first regulatory gene. According to preferred embodiments, either regulatory gene can be expressed, but both preferably are not maximally expressed simultaneously. In a first expression state, the constitutive promoter ($P_2$) is active, and the inducible promoter ($P_1$) is substantially inactive (due to the absence of a sufficient amount of an activating agent and the inhibitory effect of the second regulatory gene product).

The presence of an activating agent (X) activates the inducible promoter ($P_1$) to transition the switch of the invention to a second expression state in which the inducible promoter ($P_1$) is active and the constitutive promoter ($P_2$) is substantially inactive. However, an important feature of the invention is that a minimal threshold amount of the activating agent is required to cause the transition to the second expression state. In the presence of a threshold concentration of activating agent (X), expression from the inducible promoter ($P_1$) is sufficient to inhibit expression from the constitutive promoter ($P_2$). While the concentration of the activating agent is maintained above the threshold concentration, the second expression state is maintained. When the concentration of the activating agent falls below the threshold concentration, the first expression state is reestablished. Furthermore, the cycling of the oscillator is caused by the periodic changes in concentration of the activating agent, which in turn is regulated by periodic changes in the expression of one or more regulatory genes disposed within the oscillator (dashed lines in FIG. 1), which in turn are regulated by the expression state of the oscillator. Accordingly, the switch of the invention may transition periodically between its two expression states in the absence of exogenously added agents.

In a preferred embodiment, the activating agent which acts to induce expression from the inducible promoter of the oscillator is a protein. Expression of the activating protein preferably is under the control of an additional promoter. The expression and increase in concentration of the activating protein is coupled with the oscillator such that as the inducible promoter of the oscillator is turned "on", expression of the activating agent is turned "off". Similarly, as the inducible promoter of the oscillator is turned "off", expression of the activating agent is turned "on". This results in a switch which transitions between its two expression states in a periodic manner.

According to the invention, the inhibitory effects of the regulatory gene products expressed from the inducible and constitutive promoters is dependent on both the expression level of the gene product and the inherent inhibitory properties of the respective gene products. Expression level is a function of promoter strength, RNA stability, translational efficiency (if the gene product is a protein), post translational modification and protein stability (if the gene product is a protein). Accordingly, an activating agent that increases the expression level of the inducible regulatory gene product by increasing transcription, translation, RNA stability, post translational modification, protein stability, or a combination of the above, can cause a switch in expression states once it reaches a threshold concentration.

According to a preferred embodiment of the invention, the multi-state oscillator switch of the invention is a DNA construct comprising a network of genes such that expression of a gene of interest may be increased or decreased with regular periodicity. According to the invention, one or more genes of interest can be linked to the inducible and/or constitutive promoters of the multi-state oscillator switch of the invention. Alternatively, the gene or genes of interest may be transcribed from a separate promoter that is identical to one of the promoters in the switch or is regulated in the same way as one of the promoters of the switch.

BRIEF DESCRIPTION OF THE DRAWINGS

FIG. 3 is a schematic illustration of components of a genetic switch which alternates between two expression states.

FIGS. 4A–4B are examples of exemplary adjustable-threshold switches.

FIGS. 9A–9D are schematic illustrations of four plasmid types used to construct a toggle switch.

In FIG. 11C, cells were initially divided, diluted and induced with IPTG for 6 hours (circles) or grown without inducer (squares).

DESCRIPTION OF THE INVENTION

Figure 1:
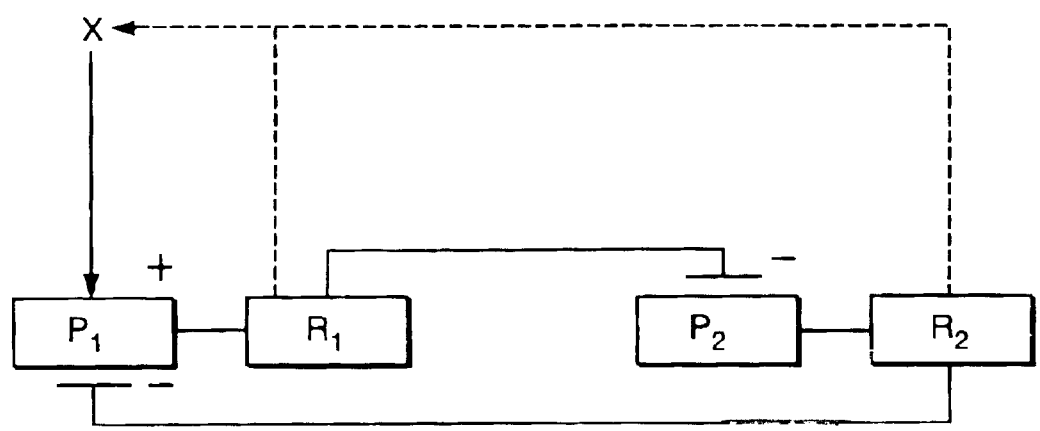
FIG. 1 is a schematic illustration of an exemplary multi-state oscillator switch of the invention.

The invention provides methods and compositions that extend the functionality of synthetic gene regulatory systems beyond that of currently available systems. Specifically, the invention provides periodic or oscillating gene regulatory systems that oscillate between two alternative states of gene expression. According to the invention, a gene of interest can be expressed periodically without the application of an external signal or stimulus. According to the invention, one or more different genes of interest can be expressed periodically. Methods and compositions of the invention are useful for the regulating gene expression, for example, in the context of gene therapy, tissue engineering, biotechnology, and biocomputing.

The oscillating constructs of the invention are based upon adjustable-threshold constructs. A typical adjustable-threshold construct includes a constitutive promoter and an inducible promoter. The constitutive promoter expresses an inhibitor of transcription from the inducible promoter, and the inducible promoter expresses an inhibitor of transcription from the constitutive promoter. An oscillating system of the invention further includes a third promoter that expresses an agent that activates the expression of the inducible promoter. In one embodiment, transcription from the third promoter is activated, either directly or indirectly, when the constitutive promoter is active. Accordingly, a self-contained cycle is established as follows. Expression from the constitutive promoter inhibits transcription from the inducible promoter but activates transcription from the third promoter. Activation of the third promoter causes expression of the activating agent. When the activating agent reaches a predetermined threshold, expression of the inducible promoter inhibits expression of the constitutive promoter. As a result, expression of the activating agent decreases. When the activating agent concentration drops below a threshold concentration, expression from the inducible promoter decreases and expression from the constitutive promoter is reestablished, thereby continuing the cycle. Oscillating gene expression constructs of the invention, including the adjustable-threshold component, are described in more detail hereinbelow.

1. Multi-State Genetic Oscillator Components

The multi-state genetic oscillator switches of the invention are similar to adjustable-threshold switches except that the activating agent rises and fills in a periodic manner thereby causing the switch to transition between its two expression states in a periodic manner. The periodic changes in the activating agent are driven by an intrinsic regulatory means of the genetic oscillator, preferably a gene product of the switch. Accordingly, the periodic switching of the switch is driven by intrinsic components of the switch and not by extraneously added switching agents. The arrangement of an adjustable-threshold switch construct is similar to that of a toggle switch construct as exemplified in PCT/US99/28592 except that one of the promoters of the adjustable-threshold construct is inducible in that expression of the gene under control of the inducible promoter requires an activating agent or agents. In addition, the toggle and threshold constructs are distinguished from each other by the function of the agent that is used to bring about the transition from one transcription state to the other. Specifically, while the agent in a toggle switch construct inhibits the expression or activity of a regulatory gene product, for example, a repressor means such as a repressor protein or nucleic acid, the agent in a threshold switch construct activates the inducible promoter. The threshold concentration of the activating agent (e.g., activator protein X) at which the transition from one transcription state to another transcription state is achieved may be manipulated, for example, by adjusting the strengths of the first and second promoters as described herein.

The regulatory gene products, activating agents, and promoters used in the adjustable-threshold switch constructs of the invention are not intended to be limited to any particular type or source. Any combination of inducible promoters (and their cognate activators) and constitutive promoters (and their cognate repressors) is suitable for use in the adjustable-threshold switch construct. Suitable promoters and cognate repressors/activators are known in the art (e.g., those contained in the Swiss-Prot protein database at http://exasy.hcuge.ch/sprot/sprot-top.html) and include those listed in Tables 1 and 2, and the eukaryotic promoters $P_{hCMV}$, $P_{HSVtk}$, and $P_{SV40}$. In addition, artificial eukaryotic activators can be constructed from DNA binding proteins fused with the activation domains such as the Herpes Simplex Virus VP16 activation domain [Gossen & Bujard (1992), supra], the human B42 activation domain [Clontech Laboratories, http://www.clontech.com], or the yeast GAL4 activation domain [Darnell, et al. (1990), supra]. A cognate inducible promoter is constructed from the DNA recognition sequence of the binding domain fused with a portion of a constitutive eukaryotic promoter.

An inducible promoter (i.e., $P_1$ in FIG. 1) of an adjustable-threshold switch construct provided herein preferably directs no expression or only low levels of expression of genes under its control in the absence of a threshold concentration of an activating agent. According to the invention, a low level of expression represents a quantity of protein expressed by the gene that preferably is not detectable by, for example, an Enzyme Linked Immunosorbent Assay (ELISA). When a background level or undetectable level of the protein is measured, this may indicate that the protein is not expressed. In addition, the adjustable-threshold switch constructs require an inducible promoter that is capable of both being activated by an activating agent (e.g., X of FIG. 1) and of being suppressed by a protein (e.g., the product of regulatory gene $R_2$ of FIG. 1). Prokaryotic and eukaryotic promoters which satisfy these criteria are known in the art (e.g., those contained in the Swiss-Prot protein database at http://exasy.hcuge:.ch/sprot/sprottop.html), and can be constructed from combinations of inducible and repressible promoters. Examples of inducible prokaryotic promoters are listed in Table 1, and examples of repressible prokaryotic promoters are listed in Table 2.

Table 1—Examples of *E. coli* inducible promoters, and activators suitable for constructing genetic switches of the invention

| ACTIVATOR | PROMOTER[1] | CO-ACTIVATOR |
| --- | --- | --- |
| AraC | Arabanose operon | Arabanose |
| CadC | $P_{cad}$ (CAD Operon) | Low pH |
| CRP | DeoP2 | CAMP |
| CynR | Cyn operon | Cyanate |
| DsdC | Dsd operon | CRP, CAMP |
| Fh1A | Formate dehydrogenase/ hydrogenase genes | Formate |
| Ma1T | MalPp | Maltose |
| MaoB | Monoamine oxidase gene | CRP, cAMP, tyramine |
| I1vY | I1vC gene | Acetolactate, acetohydroxybutyrate |
| UreR | Urease operon | Urea |

[1]Transcription from the promoters is induced in the presence of both activator and co-activator.

Table 2—Examples of *E. coli* constitutive promoters and cognate repressors, suitable for constructing genetic switches of the invention

| REPRESSOR | PROMOTER |
| --- | --- |
| ArsR | Arsenic operon |
| AscG | ASC operon[1] |
| LacI | $P_{trc}$ |
| CscR | Sucrose operon |
| DeoR (NucR) | Deoxyribose operon |
| DgoR | DGORKAT operon |
| FruR | Fructose operon |
| Ga1R | Galactose operon |
| GatR | Galactitol operon |
| CI | $P_L$ |
| LexA | SOS response regulon |
| RafR | Raffinose operon |
| TetR | Tetracycline resistance operon |
| QacR | Multi-drug resistance operon |
| PtxS | Gluconate operon |

Furthermore, the constructs provided herein are not intended to be limited to the location of regulatory gene ($R_1$) and a gene of interest (e.g., Clone) in relation to the inducible promoter $P_1$ (see FIG. 3). Rather, the constructs of the invention are expressly contemplated to encompass both $P_1$-$R_1$-Clone operons as well as $P_1$-Clone-$R_1$ operons so long as each of $R_1$ and Clone are operably linked to $P_1$. Moreover, the invention also contemplates having one gene of interest (e.g., Clone 1) operably linked to $P_1$-$R_2$ as well as another gene of interest (e.g., Clone 2) operably linked to $P_2$-$R_2$. In addition, the invention also contemplates having the first operon (e.g., $P_1$-$R_1$-Clone) and second operon (e.g., $P_2$-$R_2$) encoded by a single continuous nucleic acid sequence or as two or more nucleic acid sequences.

According to the invention, an oscillating activating means periodically switches the adjustable-threshold switch between an "on" state and an "off" state. Preferably, an oscillating amount of an activating agent causes the switch to oscillate between its alternative expression states. In a preferred embodiment, the activating agent is a gene product that is expressed periodically from a third promoter. As discussed herein, oscillating or periodic expression of the activating agent is achieved by functionally coupling its promoter activity to the expression state of the switch. The promoter for the activating agent is active when the inducible promoter of the switch is inactive and the constitutive promoter is active. In contrast, the promoter for the activating agent is inactive when the inducible promoter of the switch is active and the constitutive promoter is inactive.

In one embodiment of the invention, an activating agent is a molecule that increases transcription from the inducible promoter. In general, the expressed activating agent activates transcription by binding to double stranded DNA (dsDNA) or by activating a molecule that binds to dsDNA. In an alternative embodiment of the invention, an activating agent is a molecule that increases the expression level of a gene by increasing the translation rate of its RNA transcript. In general, an agent can increase translation by binding to RNA or by activating a molecule that binds to RNA.

It is contemplated that a variety of configurations may be useful in the practice of the invention. As discussed previously, the multi-state oscillator switch is a particular type of an adjustable-threshold switch. However, in a preferred embodiment, the oscillatory behavior is achieved by adding to the adjustable-threshold switch a feedback loop comprising one or more additional genes under the control of an additional promoter. Three preferred configurations for a multi-oscillator switch are shown in FIG. 2, which are discussed in more detail below.

Figure 2A:
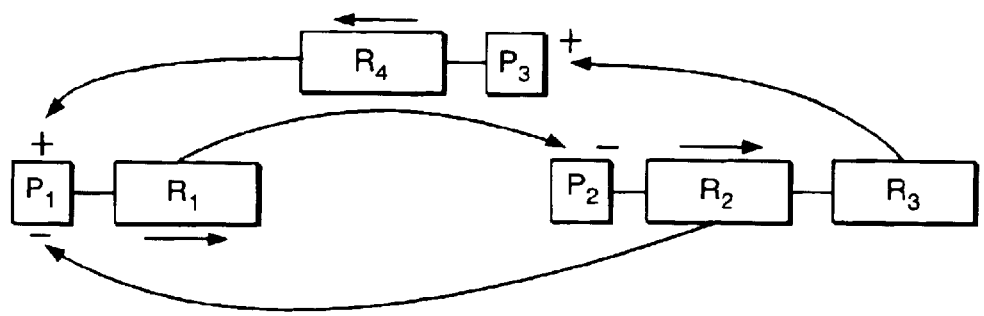
FIGS. 2A–2C are schematic illustrations of exemplary multi-state oscillator switches of the invention.

A first configuration is illustrated in FIG. 2A. The oscillator switch comprises: a first nucleic acid (e.g. DNA or RNA) construct comprising a first inducible promoter ($P_1$) operably associated with a first gene encoding a first regulatory protein ($R_1$); a second nucleic acid construct comprising a constitutive promoter ($P_2$) operably associated with a second gene encoding a second regulatory protein ($R_2$) and to a third gene encoding a third regulatory protein ($R_3$); and a third nucleic acid construct comprising a second inducible promoter ($P_3$) operably associated with a fourth gene encoding a fourth regulatory protein ($R_4$). The direction of transcription of $R_1$, $R_2$ and $R_4$ are indicated by arrows. As a result, $R_3$ is placed under the control of $P_2$ in tandem with $R_2$ (the second regulatory gene of the adjustable threshold switch). Furthermore, in this configuration $R_4$ is the activating agent for the first inducible promoter ($P_1$).

The first regulatory protein ($R_1$), when produced, is capable of repressing transcription (denoted by the "−" symbol) from the constitutive promoter ($P_2$), the second regulatory protein ($R_2$), when produced, is capable of repressing transcription from the first inducible promoter ($P_1$). The third regulatory protein ($R_3$), when produced, is capable of increasing transcription (denoted by the "+" symbol) from the second inducible promoter ($P_3$), and the fourth regulatory protein ($R_4$), when produced, is capable of increasing transcription from the first inducible promoter ($P_1$). In this embodiment, $R_1$ and $R_2$ are repressor proteins that repress transcription from $P_2$ and $P_1$, respectively. It is contemplated that $P_1$ and $P_2$, and optionally $P_3$, contain one or more operator sequences. It is contemplated that a gene of interest may be placed downstream (i.e., 3') of and under the control of $P_1$ or $P_2$. Alternatively, different genes of interest may be placed downstream and under the control of $P_1$ and $P_2$. As a result of this type of configuration, the genes of interest may be expressed in a regular and periodic manner as the concentration of the activating agent ($R_4$ in this case) increases above or falls below a threshold value necessary to induce transcription from $P_1$.

Although the first, second and third nucleic acid constructs are shown in separate nucleic acid sequences, it is contemplated that the first and second nucleic acid sequences may be disposed within a single contiguous nucleic acid sequence, the first and third nucleic acid sequences may be disposed within a single contiguous nucleic acid sequence, the second and third nucleic acid sequences may be disposed within a single contiguous nucleic acid sequence, or that all of the first, second and third nucleic acid constructs may be disposed within a single contiguous nucleic acid sequence.

Figure 2B:
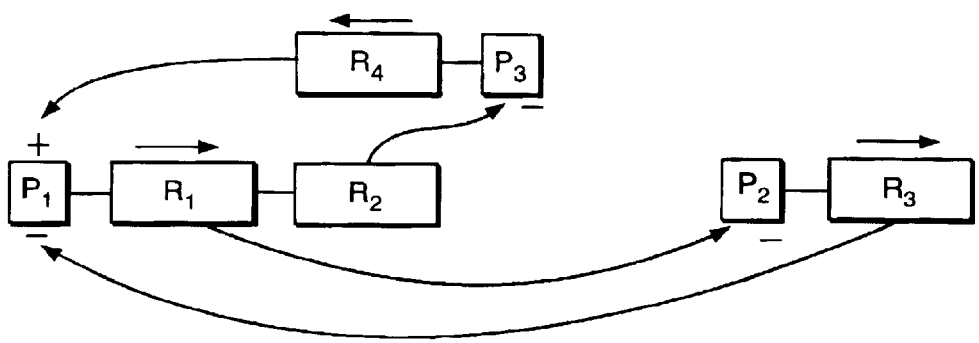

A second configuration is illustrated in FIG. 2B. The oscillator switch comprises: a first nucleic acid construct comprising an inducible promoter ($P_1$) operably associated with a first gene encoding a first regulatory protein ($R_1$) and a second gene encoding a second regulatory protein ($R_2$); a second nucleic acid construct comprising a first constitutive promoter ($P_2$) operably associated with a third gene encoding a third regulatory protein ($R_3$); and a third nucleic acid construct comprising a second constitutive promoter ($P_3$) operably associated with a fourth gene encoding a fourth regulatory protein ($R_4$). The direction of transcription of $R_1$, $R_3$ and $R_4$ are indicated by arrows. In this configuration, R4 is the activating agent for the first inducible promoter ($P_1$).

The first regulatory protein ($R_1$), when produced, is capable of repressing transcription (denoted by the "−" symbol) from the constitutive promoter ($P_2$), the second regulatory protein ($R_2$), when produced, is capable of repressing transcription from the second constitutive promoter ($P_3$) and the third regulatory protein ($R_3$), when produced, is capable of repressing transcription from the inducible promoter ($P_1$). The fourth regulatory protein ($R_4$), when produced, is capable of increasing transcription (denoted by the "+" symbol) from the first inducible promoter ($P_1$). In this embodiment, $R_1$, $R_2$ and $R_3$ are repressor proteins that repress transcription from $P_2$, $P_3$ and $P_1$, respectively. It is contemplated that $P_1$, $P_2$, and $P_3$, therefore, contain one or more operator sequences.

It is contemplated that a gene of interest may be placed downstream of and under the control of $P_1$ or $P_2$. Alternatively, different genes of interest may be placed downstream and under the control of $P_1$ and $P_2$. As a result of this type of configuration, the genes of interest may be expressed in a regular and periodic manner as the concentration of the activating agent ($R_4$ in this case) increases above or falls below a threshold value necessary to induce transcription from $P_1$.

Although the first, second and third nucleic acid constructs are shown in separate nucleic acid sequences, it is contemplated that the first and second nucleic acid sequences may be disposed within a single contiguous nucleic acid sequence, the first and third nucleic acid sequences may be disposed within a single contiguous nucleic acid sequence, the second and third nucleic acid sequences may be disposed within a single contiguous nucleic acid sequence, or that all of the first, second and third nucleic acid constructs may be disposed within a single contiguous nucleic acid sequence.

Figure 2C:
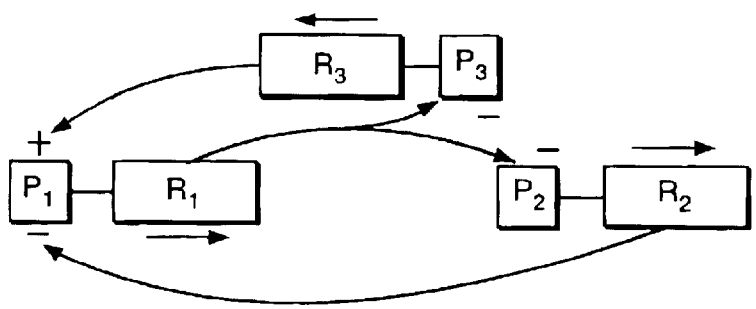

A third configuration is illustrated in FIG. 2C. The oscillator switch comprises: a first nucleic acid construct comprising an inducible promoter ($P_1$) operably associated with a first gene encoding a first regulatory protein ($R_1$); a second nucleic acid construct comprising a first constitutive promoter ($P_2$) operably associated with a second gene encoding a second regulatory protein ($R_2$); and a third nucleic acid construct comprising a second constitutive promoter ($P_3$) operably associated with a third gene encoding a third regulatory protein ($R_3$). The direction of transcription of $R_1$, $R_2$ and $R_3$ are indicated by arrows. In this configuration, $R_3$ is the activating agent for the first inducible promoter ($P_1$).

The first regulatory protein ($R_1$), when produced, is capable of repressing transcription (denoted by the "−" symbol) from the constitutive promoters $P_2$ and $P_3$, the second regulatory protein ($R_2$), when produced, is capable of repressing transcription from the inducible promoter ($P_1$). The third regulatory protein ($R_3$), when produced, is capable of increasing transcription (denoted by the "+" symbol) from the first inducible promoter ($P_1$). In this embodiment, $R_1$ and $R_2$ are repressor proteins. $R_1$ repress transcription from $P_2$, and $P_3$. $R_2$ represses transcription from $P_1$. It is contemplated that $P_1$, $P_2$, and $P_3$, therefore, contain one or more operator sequences.

It is contemplated that a gene of interest may be placed downstream or 3' of and under the control of $P_1$ or $P_2$. Alternatively, different genes of interest may be placed downstream and under the control of $P_1$ and $P_2$. As a result of this type of configuration, the genes of interest may be expressed in a regular and periodic manner as the concentration of the activating agent ($R_3$ in this case) increases above or falls below a threshold value necessary to induce transcription from $P_1$.

Although the first, second and third nucleic acid constructs are shown in separate nucleic acid sequences, it is contemplated that the first and second nucleic acid sequences may be disposed within a single contiguous nucleic acid sequence, the first and third nucleic acid sequences may be disposed within a single contiguous nucleic acid sequence, the second and third nucleic acid sequences may be disposed within a single contiguous nucleic acid sequence, or that all of the first, second and third nucleic acid constructs may be disposed within a single contiguous nucleic acid sequence.

Furthermore, in each of the configurations shown in FIGS. 2A, 2B and 2C, it is contemplated that a gene of interest may also be placed under the control of (i.e., is in operable association with) $P_3$. As a result, the level of expression of the genes of interest may also change periodically in response to changes in $P_3$ activity. In addition, different genes of interest may be placed downstream and under the control of $P_1$ or $P_2$. As a result of this type of configuration, the genes of interest may be expressed in a regular and periodic manner as the concentration of the activating agent increases above or falls below a threshold value necessary to induce transcription from $P_1$.

Preferred embodiments of the two-state oscillator constructs discussed above are characterized as being able to generate sustained periodic expression of genes in a first operon (i.e., one or more genes operably associated with $P_1$ of FIG. 2), genes in a second operon (i.e., one or more genes operably associated with $P_2$ of FIG. 2), and/or genes in a third operon (i.e., one or more genes operably associated with $P_3$ of FIG. 2) without the addition of a stimulus that is extraneous to the products of the three operons. In order to produce or modify this behavior it may be desirable to adjust the expression efficiency of the protein products as described herein. In addition, the period of the oscillations also may be manipulated.

The repressors, activators and promoters used in the periodic genetic switch constructs of the invention are not intended to be limited to any particular type or source. Any combination of inducible promoters (and their cognate activators) and constitutive promoters (and their cognate repressors) is suitable for use in the constructs of the invention. Suitable promoters and cognate repressors/activators are known in the art (e.g., those contained in the Swiss-Prot protein database at http://exasy.hcuge.ch/sprot/sprot-top.html) and include prokaryotic promoters, examples of which are listed in Tables 1 and 2, and eukaryotic promoters, examples of which are listed in Table 3. In addition, artificial eukaryotic activators can be constructed from DNA binding proteins fused with the activation domains such as the Herpes Simplex Virus VP16 activation domain [Gossen & Bujard (1992), supra], the human B42 activation domain [Clontech Laboratories, http://www.clontech.com], or the yeast GAL4 activation domain [Darnell, et al. (1990), supra]. A cognate inducible promoter is constructed from the DNA recognition sequence of the binding domain fused with a portion of a constitutive eukaryotic promoter.

An inducible promoter (i.e., $P_1$ in FIGS. 1 and 2) of a switch construct provided herein preferably directs only low levels of expression of genes under its control in the absence of the threshold concentration of activating agent. According to the invention, a low level of expression represents a quantity of protein expressed by the gene that is preferably below the threshold concentration as detected by, for example, an Enzyme Linked Immunosorbent Assay (ELISA). When a background level or undetectable level of the protein is measured, this may indicate that the protein is not expressed. In addition, the adjustable-threshold switch constructs require an inducible promoter that is capable of both being activated by an activating agent (e.g., X in FIG. 1) and of being suppressed by a protein (i.e., the expression product of regulatory gene 2 ($R_2$) of FIG. 1). Prokaryotic and eukaryotic promoters which satisfy these criteria are known in the art (e.g., those contained in the Swiss-Prot protein database at http://exasy.hcuge:.ch/sprot/sprottop.html), and can be constructed from combinations of inducible and repressible promoters.

2. Multistate Oscillator Uses

Multi-state oscillators of the invention, including two-state oscillator constructs, have clinical applications such as in gene therapy. It is understood that the concentration of certain hormones in the body fluctuates periodically during the day. Currently, treatment of diseases in which these hormones are deficient may be accomplished through the periodic ingestion of drugs in order to bring about a periodic change in the concentration of the deficient hormone. Such treatments may be achieved instead by placing the missing or damaged gene which encodes the appropriate hormone under the control of a two-state oscillator of the invention. The period of the oscillator can be adjusted appropriately such that the hormone is periodically expressed without the need for drug ingestion and such that the periodic change in the concentration of the expressed hormone mimics that of a normal state.

Two-state oscillator constructs of the invention may also be used to control cell cycle. For example, two-state oscillator constructs may be used to actively alter cell-division cycle (CDC) frequency. In active control, a construct with inherent oscillations may be coupled to the cell cycle and drive it at a new frequency. Such a function could be carried out by a two-state oscillator which periodically expresses one of the CDC proteins or a CDC binding protein. Furthermore, the frequency of the two-state oscillator, and hence, the frequency of cell division, may be dynamically controlled by modulating the time-delay in the feedback loop.

The following examples serve to illustrate certain preferred embodiments and aspects of the present invention and are not to be construed as limiting the scope thereof.

EXAMPLES

Example 1

General Considerations

In order to achieve the oscillatory properties of the multi-state oscillator, or to modify the period of oscillators of the multi-state oscillator, it may be desirable to modify the efficiency of expression of the regulatory genes in the oscillator construct. The efficiency of expression of the regulatory genes in the multi-state oscillator switch constructs may be altered in prokaryotic and eukaryotic cells by manipulating one or more of the following: the strength of RNA polymerase (RNAP) binding to DNA ($K_{mu}$ or $K_{mv}$), the maximum rate of mRNA synthesis by RNAP ($\lambda_1$ or $\lambda_2$), the strength of inhibitor binding to the DNA ($K_{iu}$ or $K_{iv}$), the strength of activator binding to DNA ($K_{mx}$), the rate of translation of mRNA into functional protein ($k_1$ or $k_2$), and the rate of protein degradation, i.e., protein stability ($d_1$). These features are further described below.

i. RNAP Binding

In prokaryotic cells, recognition of the promoter sequence by RNAP is mediated by helper proteins called sigma factors that bind to two sites in the promoter: the Pribnow box (or −10 region) and the −35 region. Typically, each of these sites has an ideal sequence called a consensus sequence. The strength of binding of sigma factors, and thus the strength of RNAP binding, is determined by how closely these regions match their consensus sequence [Darnell et al (1990), supra]. Furthermore, modifications of a region upstream of the −35 region, called the UP element, have been shown to dramatically alter the rate of transcription [Estreem, S T et al. (1998) Proc. Natl. Acad. Sci. USA 95:9761–9766; Yamada, M, et al. (1991) Gene 99:109–114]. The UP element, which has also been shown to have a consensus sequence, probably enhances the binding of the RNAP complex. By modifying the sequence of the −10, −35 and UP regions, e.g. by introducing a deletion, point mutation or insertion, the strength of RNAP binding and, hence, the promoter strength, can be altered. Relative promoter strengths can be determined be quantitative assays of the expression of reporter genes such as the green fluorescent protein (GFP), β-galactosidase ((β-gal), or chloramphenicol acetyl transferase (CAT). Thus one of skill in the art may determine whether, for example, a mutation has increased or decreased the level of expression of a gene.

ii. Transcription Elongation

Once the RNAP binds to a promoter, it opens the DNA double helix and moves forward, adding ribonucleotides to the mRNA transcript. The rate of transcription is determined partially by the nucleotide content and partially by the secondary structure (if any) of the mRNA. High guanosine and cytosine content of the mRNA tends to slow the transcription rate [Darnell et al. (1990), supra]. Furthermore, secondary structures that form in the mRNA behind the transcription complex can interfere with the transcription process [Darnell et al. (1990), supra]. Although the DNA content of the coding region cannot be substantially altered (only silent mutations alter the mRNA sequence without changing the protein properties), a leader region of mRNA may be inserted upstream of the coding region. This region can be designed to slow the rate of transcription elongation. A change in the rate of transcription elongation may be determined using methods known in the art. For example, pulse labeling mRNA transcripts with radioactive nucleotides can be used to track mRNA both temporally and spatially.

iii. Inhibitor Binding

Special sequences of DNA called operators often are found within or near a promoter. The inhibitor proteins (repressors) block transcription by binding to these operators. A given repressor or activator typically recognizes only one specific operator sequence. The affinity of the repressor/activator for the operator can be altered by modifying the operator sequence, e.g., by introducing a point mutation, insertion or deletion. Exemplary operator sequences useful in the practice of the invention include, for example, $O_{lac}$, $O_{lex}$, $O_{tet1}$, $O_{tet2}$, $O_{R1}$, $O_{R2}$, $O_{R3}$, $O_{L1}$, $O_{L2}$, and $O_{L3}$.

iv. Translation Rate

The rate of translation of mRNA into an amino-acid sequence is governed primarily by three factors: the ribosome binding site (RBS), the secondary structure of the mRNA, and the codon content of the coding region. The RBS typically is located 5–10 bases upstream of the start codon. Translation is most efficient when this sequence matches a consensus sequence called the Shine-Dalgarno (SD) sequence [Darnell et al. (1990), supra, Backman, K & Ptashne, M. (1978) Cell 13:65–71; Jacques, N & Dreyfus, M. (1990) Molecular Microbiology 4:1063–1067; Shine, J & Dalgarno, L. (1975) Nature 254:34–38]. Thus, translation rate can be altered by modifying the RBS, e.g., by introducing a point mutation, insertion or deletion. As in transcription, the formation of secondary structures by the mRNA can interfere with translation machinery. Thus, modification of the leader region of the mRNA or introduction of silent mutations into the coding region may be used to change translation rate. Finally, in various organisms certain codons are favored, i.e., tRNAs for certain codons are more abundant than others. Translation is more efficient when the favored codons are used [Jacques & Dreyfus (1990), supra]. Thus, a coding region can be optimized by introducing silent mutations that utilize the favored codons.

v. Protein Stability

The stability of a protein can be altered by introducing mutations into the amino acid sequence that make the protein more or less resistant to denaturation or proteolytic degradation. Powerful experimental techniques such as directed evolution, DNA shuffling and two-hybrid screening are known in the art and may be used to rapidly screen large numbers of mutant proteins for the desired stability characteristics. In addition, protein degradation rate may be altered by attaching a short, organism-specific, oligonucleotide sequence [Andersen et al. (1998) Appl. Environ. Microbiol. 64:2240–2246] to the 3' end of the gene which encodes the protein. This sequence targets the encoded protein for rapid degradation by the cell.

Design Considerations For Prokaryotic Cells

In one preferred embodiment, the cell containing the genetic cassettes of the invention is a prokaryotic cell. Preferred prokaryotic host cells include, for example, *Escherichia coli, Bordetella pertussis, Bacillus subtillis, Salmonella typhimurium,* and *Staphylococcus aureus.* However, *E. coli* is most preferred.

Constructs containing multi-state oscillators which function in other prokaryotic cells are expressly contemplated to be within the scope of the invention. Oscillators that contain *E. coli* promoters may function without modification in related bacterial species such as gram-negative bacteria, or may be readily be modified to bring about transcription of a gene of interest.

A multi-state oscillator construct is an extension of the adjustable-threshold switch, which in turn is similar to a bistable genetic toggle construct described in PCT/US99/28592. FIG. 3 is a schematic illustration of a toggle switch of PCT/US99/28592 that is similar to the adjustable-threshold switch and multi-state oscillator constructs. Promoter 1, $P_1$, and promoter 2, $P_2$, are strong constitutive promoters from the selected host organism (prokaryotic or eukaryotic). Gene I encodes a repressor protein that binds to the $O_2$ operator site and represses transcription from $P_2$. Gene 2 encodes a repressor protein that binds to the $O_1$ operator site and represses transcription from $P_1$. Open arrows indicate direction of transcription. An additional gene or genes of interest ("Clone") is placed under the control of $P_1$, i.e. is in operable association with $P_1$. In this configuration, $P_1$ and $P_2$ are constitutively transcribed in the selected host organism, but lack regulatory sequences needed to repress expression. These regulatory sequences are provided by the operator sites spliced within or downstream of the constitutive promoters. The operator sites, which can be derived from any E. coli promoter or from a promoter in the host organism, bind their associated repressor protein encoded by Gene 1 or Gene 2. Thus, in this case, two fusion promoters are created that are efficiently transcribed in the host organism and repressed by the selected E. coli repressors, or by a repressor chosen from the host organism. This same scheme can be applied to a multi-state oscillator switch construct to produce a construct that is functional in any selected organism. However, in the adjustable-threshold switch and multi-state oscillator constructs of the invention, promoter 1 rather than being a constitutive promoter is an inducible promoter. In addition, in the multi-state oscillator construct, additional promoters and regulatory genes that provide feedback expression of the activating agent are included.

To construct a multi-state oscillator construct of the invention, any repressor protein may be used so long as it reduces transcription by its cognate promoter. Similarly, any activating agent may be used so long as it increases transcription by the inducible promoter. Prokaryotic repressor-promoter-activating agent combinations which are suitable for use in the adjustable-threshold switch and multi-state oscillator constructs are known in the art, such as those described in the Swiss-Prot protein database [Annotated Protein Sequence Database; http://expasy.hcuge.ch/sprot/sprottop.html].

Design Considerations For Eukaryotic Cells

It is contemplated that eukaryotic cells may be used to harbor the adjustable threshold switches of the invention. Preferred eukaryotic cells include for example, mammalian cells (including human cells). Particularly preferred eukaryotic cells include myeloma cells, fibroblast 3T3 cells, monkey kidney or COS cells, chinese hamster ovary (CHO) cells, mink-lung epithelial cells, human foreskin fibroblast cells, human glioblastoma cells, teratocarcinoma cells, HER 293 cells, L929 cells, and Hela cells.

Constitutive eukaryotic promoters typically comprise two elements: the minimal promoter sequence, for example from base pairs +1 to −65, and an enhancer sequence encompassing several hundred base pairs upstream of the minimal promoter. The minimal promoter sequence contains the TATA box consensus sequence and is necessary but not sufficient for RNA polymerase II binding and transcription. In the absence of the enhancer the minimal promoter typically does not efficiently initiate transcription (Darnell, J., et al. (1990) supra, Gossen. & Bujard, J. (1992) supra; Lubon, H., et al. (1989) Molecular and Cell Biology, 9: 1342–1345; Thomsen, D R., et al. (1984) supra.] Thus, a strong eukaryotic constitutive promoter requires both a minimal promoter region and an upstream enhancer region. Exemplary strong constitutive eukaryotic promoters which direct efficient transcription in the absence of an activator and which lack an operator sequence are known in the art (e.g., those disclosed in the Swiss-Prot protein database) and exemplified by those listed in Table 3.

Table 3—Examples of Strong Constitutive Eukaryotic Promoters

| Promoter | Parent Organism/Gene |
| --- | --- |
| $P_{hCMV}$ | Human Cytomegalovirus Immediate Early Promoter [Gossen, M. & Bujard, H. (1992); Gossen, M., et al. (1995)] |
| $P_{HSVtk}$ | Herpes Simplex Virus Thymidine Kinase Promoter [Smith, GM., et al. (1988) EMBO J., 7: 3975–3982] |
| $P_{SV40}$ | Simian Virus Early Promoter [Wildeman, AG. (1988)] |
| $P_{EF-1a}$ | Human [Takeuchi, Y., et al. (1999) Mar. Biotechnol., 1(5):448–0457] |
| RSV-LTR | Rat Sarcoma Virus Promoter [Franz, WM., et al. (1997) Cardiovasc. Res., 35(3):560–6] |
| Keratin 6 | Human [Mazzalupo, S. et al. (2001) Mech. Dev., 100:65–69] |

While the promoters in Table 3 direct efficient transcription, these promoters typically are not repressed because they lack an operator sequence. Thus, in order to repress the exemplary promoters in Table 3, operator sequences preferably are operably linked to the promoter sequence.

In the absence of the enhancer, transcription may be efficiently induced by an activator protein that binds to a region upstream of the minimal promoter. Eukaryotic activator proteins typically consist of two functionally distinct and separable domains: the DNA binding domain (BD) which recognizes a specific sequence, and an acidic activation domain (AD) which stimulates transcription initiation. Any DNA binding protein may be fused to the AD to create an artificial activator protein [Smith, G M. (1988) supra]. As described below, this unifying feature of eukaryotic gene regulation facilitates the construction of eukaryotic versions of the multi-state oscillator switches.

To construct a eukaryotic version of the multi-state oscillator, constitutive eukaryotic promoters that are also repressible by a repressor protein are required. It has been previously shown that hybrid eukaryotic promoters (i.e., promoters composed of a constitutively transcribed eukaryotic promoter and a bacterial operator sequence) both are efficiently transcribed in the absence of the associated bacterial repressor protein, and are effectively repressed in the presence of the bacterial repressor. For example, a hybrid promoter has been constructed by splicing the E. coli LexA operator sequence into the HSV tk promoter. Expression from this promoter was reduced 10-fold in mammalian cells that synthesized the E. coli LexA repressor protein [Smith, G M. (1988) supra].

To construct a eukaryotic version of the multi-state oscillator switch, inducible eukaryotic promoters also are required. Construction of such inducible promoters is facilitated by the modular design of eukaryotic promoters. The enhancer domain from a constitutive eukaryotic promoter can be replaced with a DNA sequence recognized by the binding domain of the desired activator protein. Any E. coli DNA binding protein such as those listed in Table 1 may be used as the binding domain of an activator protein. For example, the DNA binding protein may be fused with an activation domain such as the HSV VP16 domain.

Because the fusion protein containing the binding domain and the activation domain is an artificial construct, it must be included in the multi-state oscillator construct. This can be accomplished by, for example, operably linking the gene for the fusion protein to a constitutive promoter which exists on the same vector as the multi-state oscillator switch, or on a different vector.

A generic scheme for constructing a eukaryotic adjustable-threshold switch construct is illustrated in FIG.

4A. Transcription of Gene 1 from $P_{min}$ is activated by a fusion protein composed of an $O_A$-binding domain and an acidic activation domain. Activation by the activator protein may be positively or negatively modulated by a chemical signal (Input). $P_{min}$ is simultaneously inhibited at operator site, $O_1$, by the bacterial repressor protein encoded by Gene 2. Promoter 2, $P_2$, efficiently transcribes Gene 2 unless inhibited at operator site $O_2$ by the bacterial repressor protein encoded by Gene 1. Open arrows indicate direction of transcription. Clone is an additional gene or genes which may be placed under the control of $P_{min}$ or optionally under the control of $P_2$.

An exemplary adjustable-threshold switch construct containing the tetO operator sequence, the $P_{minhCMV}$ promoter, the $P_{hCMV}$ promoter, the lexA gene, and the lacI gene is shown in FIG. 4B. Transcription of the lexA gene from the minimal Human Cytomegalovirus Immediate Early Promoter, $P_{minhCMV}$, is activated by the HSV-VP16:TetR fusion protein which binds at the tetO operator site. The HSV-VP16:TetR fusion protein is synthesized from the $P_{hCMV}$ promoter contained in a separate construct. Activation by the HSV-VP16:TetR can be positively or negatively modulated by a doxycycline, a tetracycline derived compound. $P_{minCmv}$ is simultaneously inhibited at operator site, $O_{lac}$, by the bacterial Lac repressor protein encoded by lacI. The constitutive promoter, $P_{hCMV}$, efficiently transcribes the lacI gene unless inhibited at operator site, $O_{lex}$, by the bacterial LexA repressor encoded by lexA. Open arrows indicate direction of transcription. Clone is an additional gene or genes which may be placed under the control of $P_{minCMV}$ or optionally under the control of $P_{hCMV}$. Furthermore, the HSV-VP16:TetR fusion protein may be designed such that doxycycline (a tetracycline derivative) acts as an inhibitor or, alternately, a co-activator of transcription initiation. [Resnitzky et al. (1994) Mol. Cell. Biol., 14:1669; Gossen et al. (1995) Science, 268: 1766]. Thus, this construct may be activated or inactivated by doxycycline. In the construction of a multi-state oscillator, external control by doxycycline is not required. However, the components of this exemplary adjustable-threshold switch also may be used to create a multi-state oscillator construct.

Transfer of an Multi-State Oscillator Switch and a Gene of Interest Into a Cell

A genetic switch, and the genes of interest to which it is operably linked, may be inserted into any of several types of DNA vectors used to transfer DNA into a cell. Examples include linear DNA, plasmid DNA, shuttle vectors, modified viruses and artificial chromosomes. The vector containing the genetic switch may then be introduced into any prokaryotic or eukaryotic cell using any one of several methods including naked DNA uptake, receptor-mediated endocytosis, viral infection, lipofection, DEAE-Dextran transfection, calcium chloride transformation, calcium phosphate transfection, and electroporation. Once the vector is introduced into a cell, it may be stably maintained in the cell by applying a appropriate selective agent including, for example, neomycin, zeocin, ampicillin, and kanamycin. In other circumstances, for example, when the requisite genes are incorporated into the genome of the host cell by, for example, homologous recombination, selective agents may not be required.

Example 2
Mathematical Analysis of Multi-State Oscillator Switches

As discussed above, an adjustable-threshold switch is an integral component of a multi-state oscillator switch of the invention. An important feature of the adjustable-threshold switch is the requirement of a threshold concentration of activating agent below which the inducible promoter is substantially inactive. The inducible promoter is activated (switched on) when the concentration of the activating agent is equal to or greater than the threshold concentration. In a preferred embodiment of the invention, the inducible promoter is substantially maximally activated by a threshold concentration of activating agent. Accordingly, a preferred adjustable-threshold switch of the invention can adopt one of two alternative states: i) an inactive "off" state in the absence of activating agent or in the presence of sub-threshold concentrations of activating agent, or ii) an active "on" state in the presence of threshold or greater than threshold concentrations of activating agent.

Many of the features of a switch between alternative expression states of an adjustable-threshold genetic switch can be illustrated by a switch between alternative expression states of a genetic toggle switch. As discussed above, an adjustable-threshold switch preferably has a configuration of genetic elements that is similar to that of a genetic toggle switch. However, in contrast to the constitutive promoters of a genetic toggle switch, the inducible promoter of an adjustable-threshold switch is only active in the presence of a threshold or greater than threshold concentration of activating agent. Despite this important difference, the dynamics of a switch to the active state, induced by a threshold concentration of activating agent, are analogous to the dynamics of a switch from a first stable state to second stable state of a genetic toggle switch, induced by a switching agent. Similarly, when the activating agent drops below its threshold concentration, the dynamics of inactivation are similar to the dynamics of a switch between alternative expression states of a genetic toggle switch.

The following mathematical analysis illustrates predicted switching dynamics for an adjustable-threshold switch, and provides a model for a multi-state oscillator wherein the concentration of the activating agent oscillates between sub-threshold and threshold concentrations, thereby causing the adjustable-threshold switch to oscillate between alternative expression states. The exemplary equations are based on a model analysis of genetic toggle and adjustable-threshold genetic switches. The experimental examples that follow the mathematical analysis illustrate the existence of two alternative expression states for genetic toggle switch constructs. According to the invention, adjustable-threshold switches similarly exhibit alternative expression states which form the basis of multi-state oscillators of the invention.

Mathematical Analysis of an Adjustable-Threshold Switch

A genetic switch with an adjustable switching threshold is produced by modification of the toggle switch design described in PCT/US99/28592. This device comprises two mutually inhibitory genes (regulatory genes), one transcribed by an inducible promoter (promoter 1), and one transcribed by a constitutive promoter (promoter 2). Transcription of each regulatory gene is inhibited by the presence of the product of the other gene. Promoter 1, because it is inducible, cannot transcribe regulatory gene 1 ($R_1$ of FIG. 1) without aid of an additional activator agent. Thus, in the absence of the activating agent (e.g., protein X of FIG. 1), constitutive promoter 2 will dominate promoter 1 and regulatory gene 2 ($R_2$ of FIG. 1) will be expressed. As the concentration of the activating agent X rises, the strength of promoter 1 rises as well. Eventually, the strength of promoter 1 exceeds that of promoter 2 and the device abruptly switches to the expression of regulatory gene 1. By manipulating the relative strengths (as described herein) of promoter 1 (when activated) and promoter 2, the concentration of the activator agent at which this transition occurs can be altered. An adjustable-threshold switch construct can be modeled using the following pair of equations (i) and (ii)

$$\frac{du}{dt} = \frac{k_1\lambda_1/\delta_1 x^\eta}{x^\eta + K_{mx}^\eta(1 + v^\gamma/K_{iv}^\gamma)} \quad \text{(i)}$$

$$\frac{dv}{dt} = \frac{k_2\lambda_2/\delta_2}{1 + K_{mv}(1 + u^\beta/K_{iu}^\beta)} - d_1 v \quad \text{(ii)}$$

where,
u=concentration of gene product of regulatory gene 1,
v=concentration of gene product of regulatory gene 2,
$\lambda_1$=maximum rate of synthesis of gene 1 mRNA by RNA polymerase,
$\lambda_2$=maximum rate of synthesis of gene 2 mRNA by RNA polymerase,
$\delta_1$=rate of degradation of gene 1 mRNA,
$\delta_2$=rate of degradation of gene 2 mRNA,
$k_1$=rate of synthesis of gene product of regulatory gene 1 by the ribosome,
$k_2$=rate of synthesis of gene product of regulatory gene 2 by the ribosome,
$K_{mu}$=Michaelis constant for RNAP binding and transcription of regulatory gene 1,
$K_{mv}$=Michaelis constant for RNAP binding and transcription of regulatory gene 2,
$K_{iu}$=equilibrium constant for inhibitory binding of gene product of regulatory gene 1 to promoter 2,
$K_{iv}$=equilibrium constant for inhibitory binding of gene product of regulatory gene 2 to promoter 1,
$d_1$=rate of degradation of gene products of regulatory genes 1 and 2,
$\beta$=cooperativity of binding of gene product of regulatory gene 1,
$\gamma$=cooperativity of binding of gene product of regulatory gene 2,
x=concentration of transcriptional activator of promoter 1,
$K_{mx}$=Michaelis constant for activator binding and transcription of regulatory gene 1,
$\eta$=cooperativity of binding of transcriptional activator.

The equations are based on the assumption that gene expression can be modeled using the law of mass action. Although gene expression typically does not involve a large number of particles, considerable evidence exists that such approximations provide a reasonable description of gene expression. For example, earlier work using a reconstituted enzyme system [Schellenberger et al., Adv. Enzyme Regul. 19, 257–284 (1980)] demonstrated the effectiveness of non-linear mathematics in predicting novel qualitative behaviors, including multistability and hysteresis, in biochemical reaction networks. In addition, a variety of physical and mathematical approaches, including logical or [Glass et al., J. Theor. Biol. 54, 85–107 (1975); Glass & Kauffman, J. Theor. Biol. 39, 103–129 (1973); Kauffman, J. Theor. Biol. 44, 167–190 (1974); Thomas, J. Theor. Biol. 73, 631–656 (1978); Thomas, J. Theor. Biol. 153, 123 (1991)], piece-wise linear [Tchuraev, J. Theor. Biol. 151, 71–87 (1991)], non-linear [Arkin & Ross, Biophys. J. 67, 560–578 (1994); Bhalla & Iyengar, Science 283, 381–387 (1999); Glass, J. Chem. Phys. 63, 1325–1335 (1975)], statistical-mechanical [Shea & Ackers, J. Mol. Biol. 181, 211–230 (1985); Smith et al., Math. Biosci. 36, 61–86 (1977)] and stochastic [Arkin et al, Genetics 149, 1633–1648 (1998); McAdams & Arkin, Proc. Natl. Acad. Sci. USA 94, 814–819 (1997); McAdams & Arkin, Annu. Rev. Biophys. Biomol. Struct. 27, 199–224 (1998)] formulations of the underlying biochemical dynamics, have had varying degrees of success in describing the behavior of gene networks.

The first term in each equation describes the synthesis of nascent proteins. Both transcription by the RNA polymerase and translation by the ribosome are included in the first term. Transcription, modeled with Michaelis-Menton kinetics, is competitively inhibited by the opposing gene product. Inhibition is achieved by the binding, as a homo-multimer, of one gene product to one or more sites in the opposing gene's promoter region. The multimeric interaction and the multiple binding sites are accounted for by the cooperativity exponents $\beta$ and $\gamma$ in the first term of each equation.

The second term describes the rate of degradation of proteins. In E. coli, the dilution of proteins as a result of cell growth is assumed to be the major determinant of the degradation rate. Since this rate is assumed to be identical for all proteins in the cell, a single rate constant, $d_1$, is used in the model for protein degradation. However, the assumption of a single rate constant is not necessary for a functional adjustable-threshold switch. The threshold switching behavior will exist in the adjustable-threshold switch with unequal degradation rates of the proteins, but an adjustment in the promoter strengths, $\alpha_1$ and $\alpha_2$, may be necessary to maintain the threshold as described below. Additional assumptions, implicit in this model, are (i) mRNA turnover is rapid, and (ii) translation of each mRNA transcript occurs at its maximum rate, i.e. proteins are rapidly synthesized from the mRNA by an excess of ribosomes. These assumptions are supported by studies of transcription and translation [Alberts, B et al. (1994) Molecular Biology of the Cell, Garland Publishing, Inc., New York; Darnell, J et al. (1990) Molecular Cell Biology, Scientific American Books, Inc., New York].

The parameters x, $K_{mx}$, and $\eta$ describe the activation of transcription by protein X. It is assumed that the activator, like the inhibitor proteins, can bind to DNA cooperatively and the activation can be modeled with Michaelis-Menton kinetics. In this model, protein X can be considered as the "input" to the switch. Increasing the concentration of protein X will cause the "output" of the switch to flip from regulatory gene 2 expression to regulatory gene 1 expression.

Figure 5:
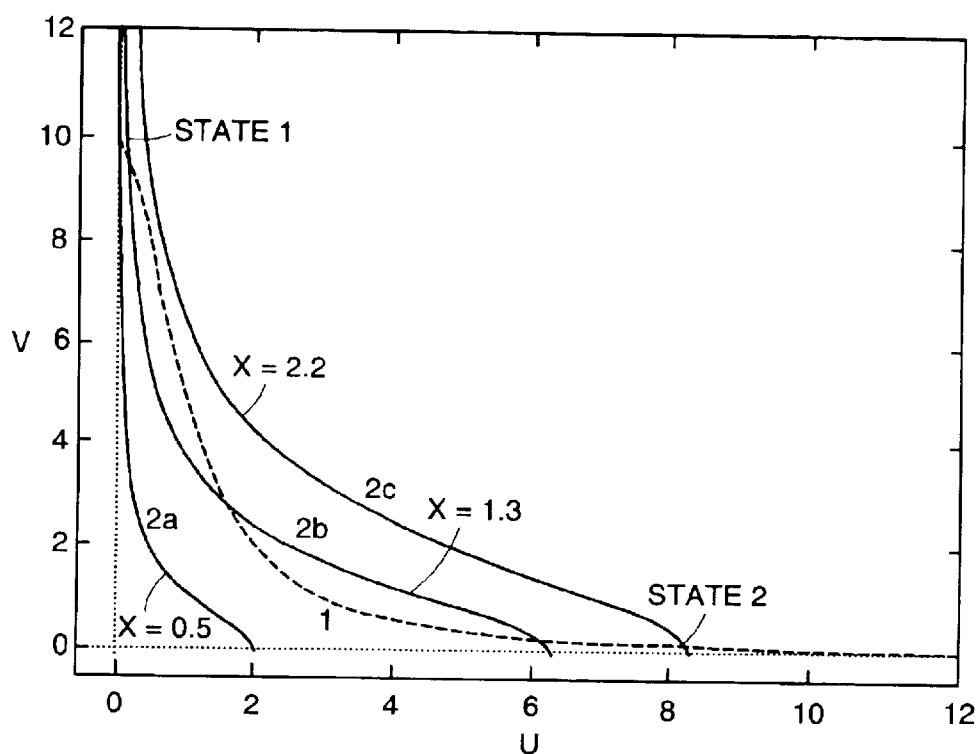
FIG. 5 is a phase plane diagram for an exemplary adjustable-threshold switch construct.

FIG. 5 provides an understanding of the switching mechanism. The dashed line is nullcline for dv/dt-0. The solid lines are nullclines for du/dt-0 for different concentrations of the transcriptional activator of promoter 1 (x). For x-0.5, state 1 is the only stable fixed point. As x increases, the system remains in state 1 until x is approximately 2. A bifurcation eliminates state 1 and the system switches dramatically to state 2.

The initial state of the system, state 1 (i.e., no activator protein, expression of regulatory gene 2, suppression of regulatory gene 1), is the stable fixed point which occurs at the intersection of nullcline 2a with nullcline 1. When the concentration of x rises, the shape of nullcline 2a is altered to nullcline 2b, causing it to intersect with nullcline 1 in two additional places. In this intermediate state, the system exhibits bi-stability analogous to that of the toggle switch construct of PCT/US99/28592. However, the system remains in state 1 in the absence of a large perturbation. As described below, this bi-stability leads to hysteresis in the switching mechanism. Depending on the intended application, hysteresis may or may not be useful. Tuning the system (e.g., by manipulating the strengths of promoter 1 ($\alpha_1$) and of promoter 2 ($\alpha_2$) as described below) allows the size of this hysteresis to be adjusted. When the concentration of x is further increased, the nullcline shifts to curve 2c, the stable fixed point at state 1 disappears and state 2

(expression of regulatory gene 1, suppression of regulatory gene 2) becomes the sole stable fixed point. Thus, the system dramatically shifts from state 1 to state 2. This shift, which is driven by the change in concentration of x, is the threshold of the system. It can be altered by adjusting the nullclines whose shape and location are determined by the parameters in equations (i) and (ii).

Analysis of this system can be simplified by rescaling time and non-dimentionalizing the variables. Equations (i) and (ii) are thus reduced to the following pair of equations (iii) and (iv):

$$\frac{d\hat{u}}{d\tau} = \frac{\alpha_1 \hat{x}^\eta}{\hat{x}^\eta + 1 + \hat{v}^\beta} - \hat{u} \quad \text{(iii)}$$

$$\frac{d\hat{v}}{d\tau} = \frac{\alpha_2}{1 + \hat{u}^\gamma} - \hat{v} \quad \text{where,} \quad \text{(iv)}$$

$$\tau = d_1 t,$$

$$\hat{u} = \frac{u}{K_{iu}(1/K_{mv} + 1)^{1/\beta}},$$

$$\hat{v} = \frac{v}{K_{iv}},$$

$$\hat{x} = \frac{x}{K_{mx}},$$

$$\alpha_1 = \frac{k_1 \lambda_1 / \delta}{d_1 K_{iu}(1/K_{mv} + 1)^{1/\beta}} \quad \text{and}$$

$$\alpha_2 = \frac{k_2 \lambda_2 / \delta_2}{d_1 K_{iv}(1 + K_{mv})}$$

Nine parameters in the original equations are collapsed into two dimensionless parameters $\alpha_1$ and $\alpha_2$. These parameters describe the efficiency (i.e. the maximum strength) of gene expression achieved by the constitutive and inducible promoters. Since they incorporate multiple parameters, including the rate of transcription, translation and degradation of the regulatory proteins in the adjustable-threshold switch, $\alpha_1$ and $\alpha_2$ may be considered the "effective promoter strength" of the constitutive and inducible promoters. By condensing nine parameters into just two parameters describing the effective promoter strength, the analysis of the effects of only five parameters (i.e., x, $\alpha_1$, $\alpha_2$, $\eta$, and $\gamma$) is required. As used herein, promoter strength is considered to be synonymous with "effective promoter strength."

Figure 6A:
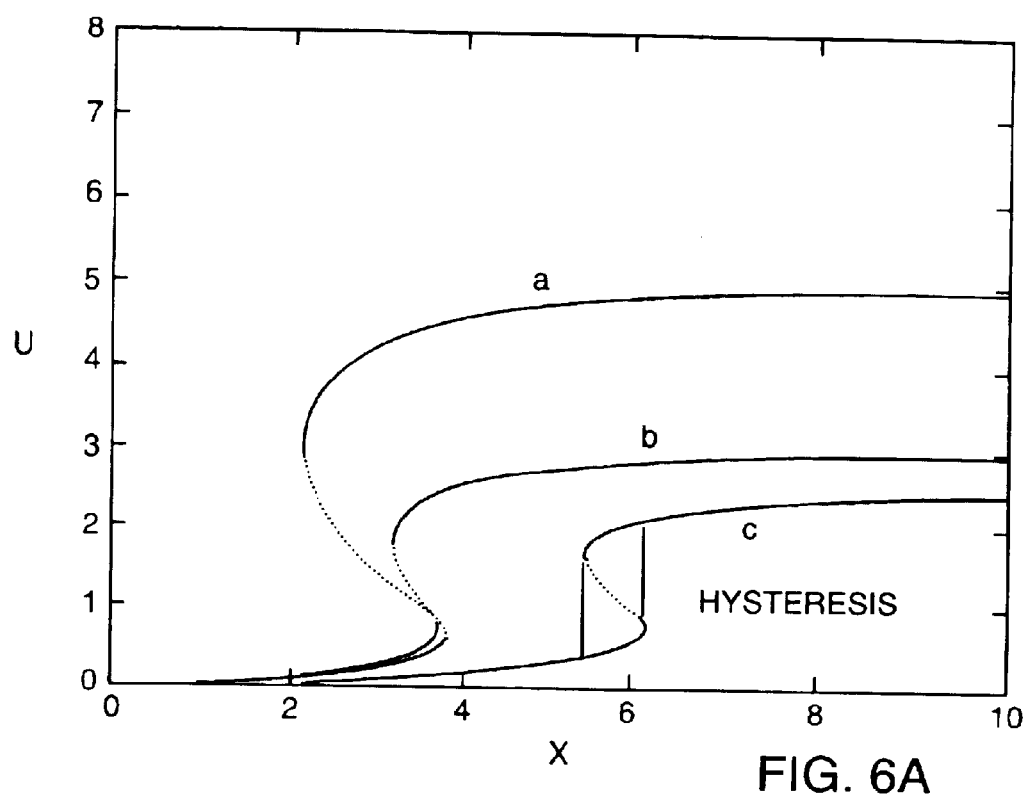
FIGS. 6A–6B are graphs showing the structure of the threshold in exemplary adjustable threshold switches.
Figure 6B:
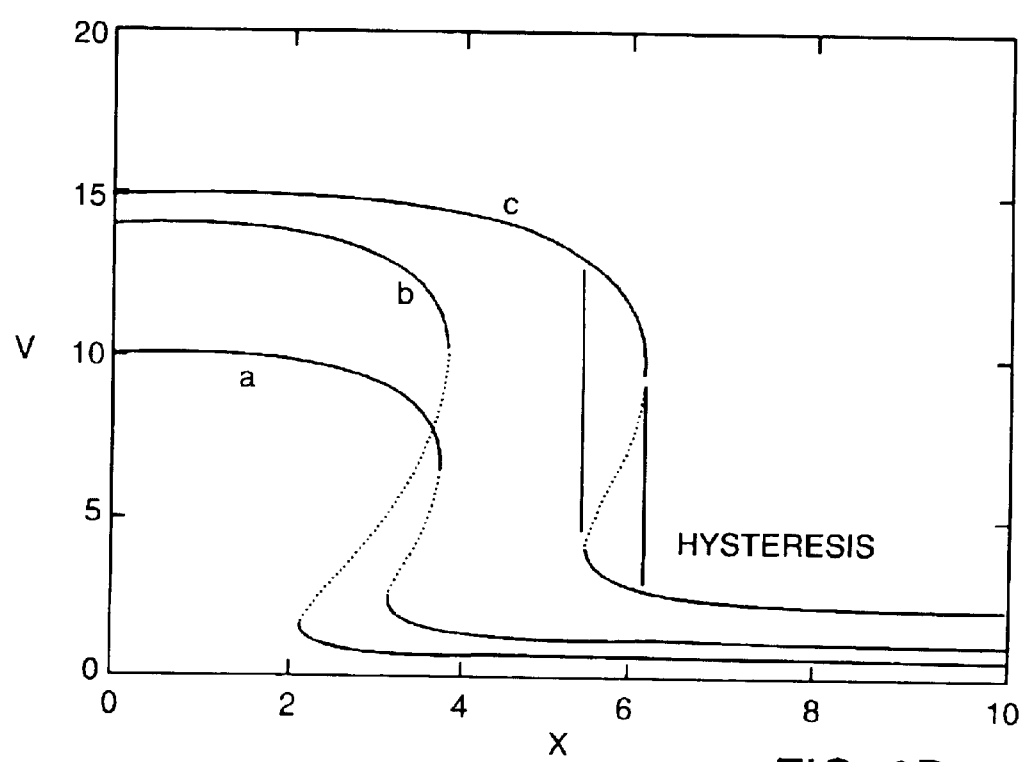

FIG. 6 shows the structure of the threshold. FIG. 6A shows the concentration of gene product of regulatory gene 1 (u) as a function of activator (A) concentration. FIG. 6B shows the concentration of gene product of regulatory gene 2 (v) as a function of activator (x) concentration. Hysteresis exists at the switching threshold as indicated by the arrows in FIGS. 6A and 6B. Both the location of the threshold and size of the hysteresis can be manipulated independently. Parameter values: $\alpha_1=5$, $\alpha_2=14$ (curve a in FIGS. 6A and 6B), $\alpha_1=3$, $\alpha_2=10$ (curve b in FIGS. 6A and 6B), $\alpha_1=2.7$, $\alpha_2=15$ (curve c in FIGS. 6A and 6B), $\eta=\gamma=2$ (all curves in FIGS. 6A and 6B). FIG. 6 shows the steady state concentrations of proteins u and v versus the concentration of x for several values of parameters $\alpha_1$, and $\alpha_2$. This figure reveals more clearly the nature of the threshold and the associated hysteresis. It also demonstrates that both the location of the threshold and the size of the hysteresis can be tuned.

Figure 7A:
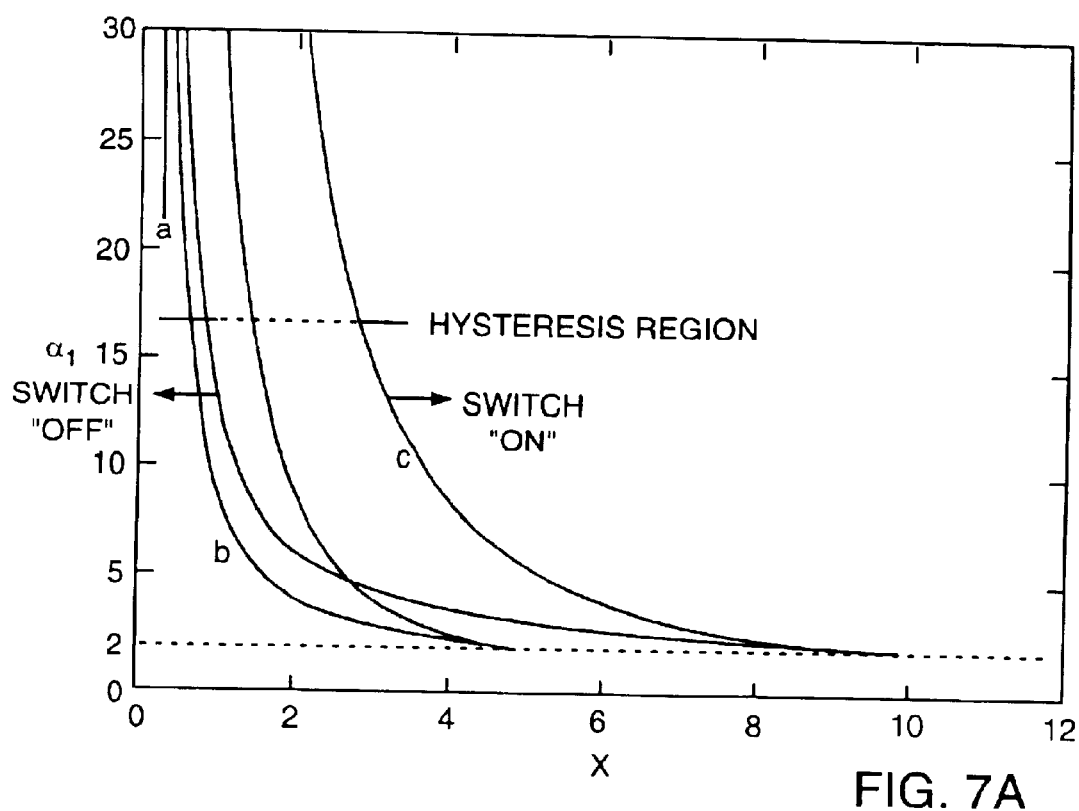
FIGS. 7A–7B are graphs showing the size of the hysteresis and the location of the threshold for a range of promoter strengths for $\alpha_1$ (FIG. 7A) and $\alpha_2$ (FIG. 7B) in an exemplary adjustable-threshold switch.
Figure 7B:
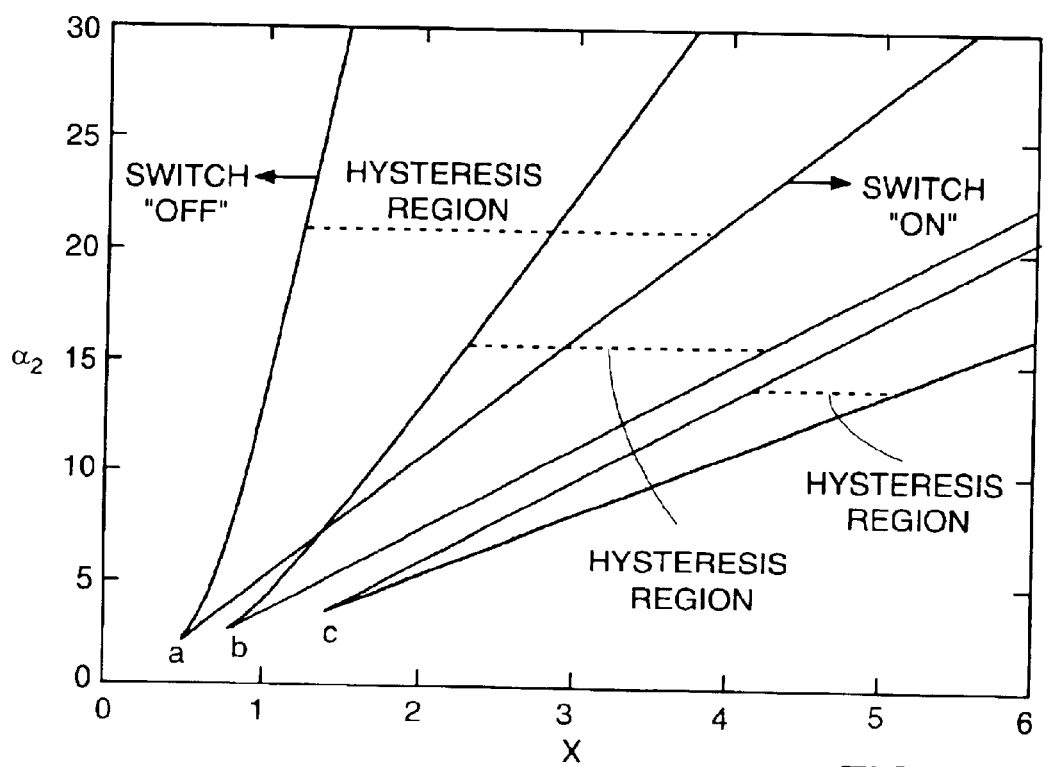
Figure 8A:
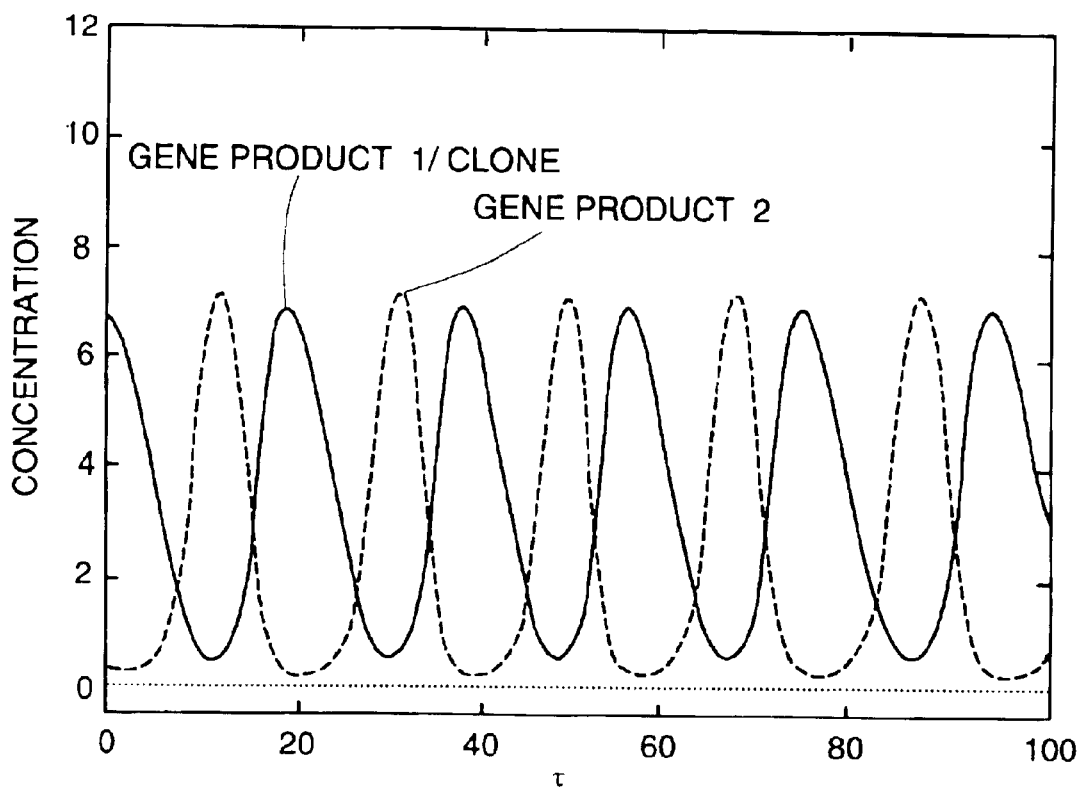
FIGS. 8A–8D are graphs showing the behavior of a two-state oscillator construct under different conditions. The behavior of the two-state oscillator construct of FIG. 2A is shown having a Time-delay: $k_d=5$ (FIG. 8A), and a Time-delay: $k_d=10$ (FIG. 8B); The behavior of the two-state oscillator construct of FIG. 2C is shown having a Time-delay: $k_d=8$ (FIG. 8C), and a Time-delay: $k_d=16$ (FIG. 8D).
Figure 8B:
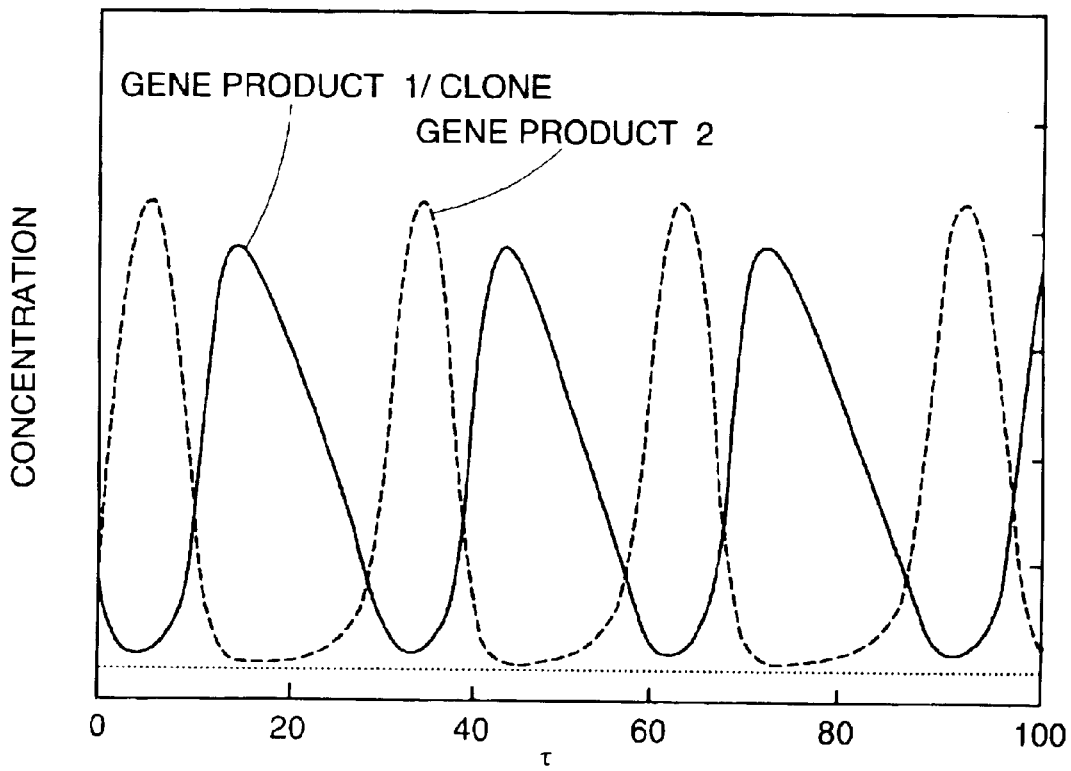
Figure 8C:
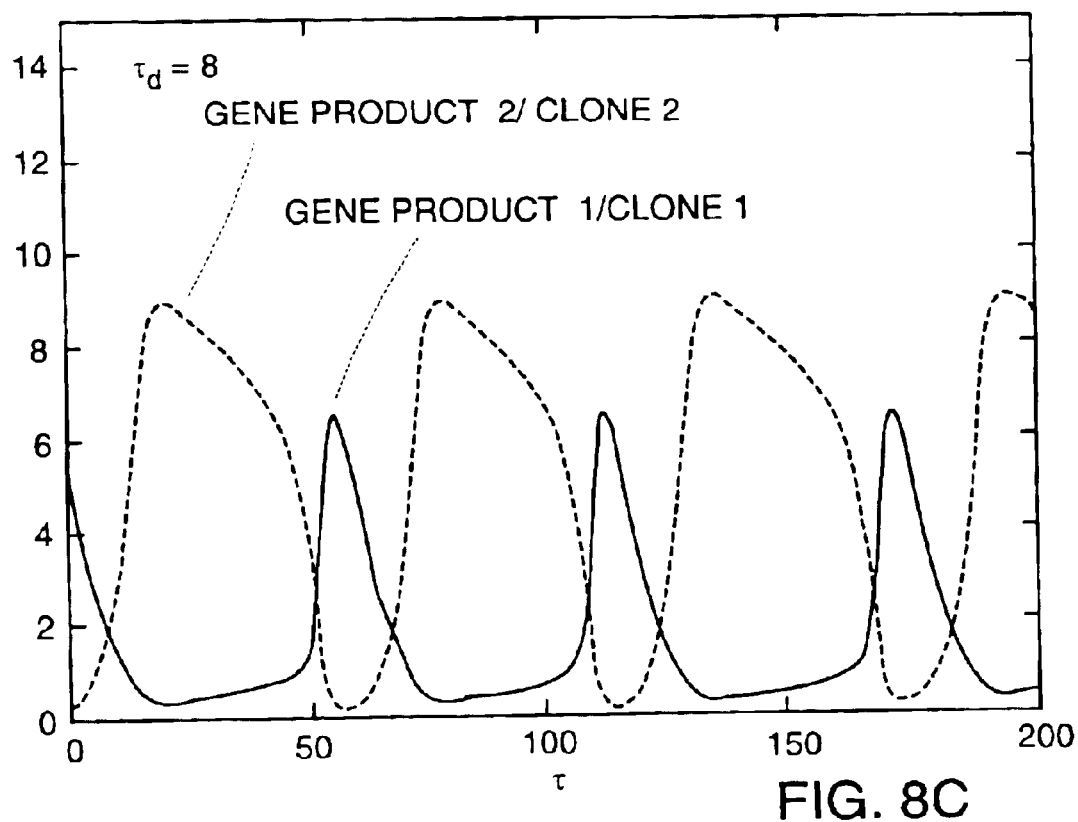
Figure 8D:
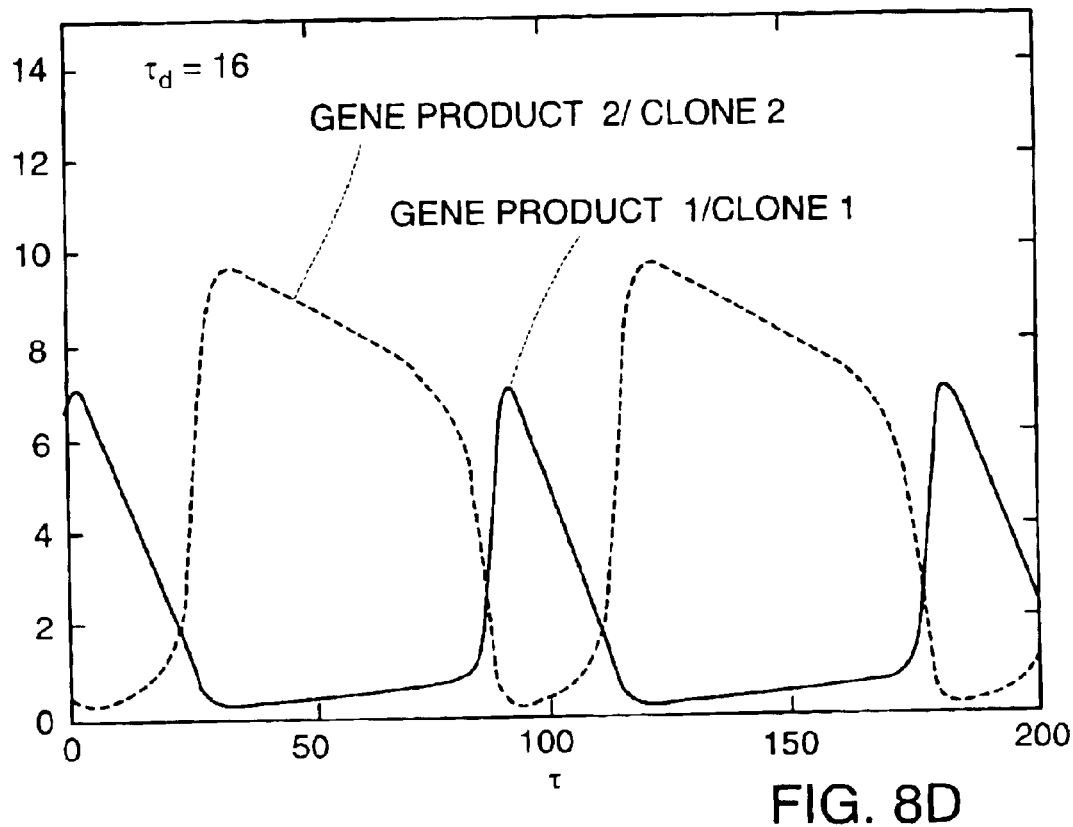

The effects of parameters $\alpha_1$ and $\alpha_2$ on the threshold and hysteresis are more fully illustrated in FIG. 7. FIG. 7A shows $\alpha_1$ as a function of activator (x) concentration and FIG. 7B shows $\alpha_2$ as a function of activator (x) concentration. FIG. 7 is a bifurcation diagram showing the size of the hysteresis and the location of the threshold for a range of values of promoter strengths in an adjustable-threshold switch construct. In FIGS. 7A and 7B, the lines demarcating the hysteresis region represent saddle-node bifurcations. To achieve minimal hysteresis, a weak promoter 1 is desirable; however, a minimal promoter strength exists beyond which no threshold will be generated. This minimal strength can be determined through experimental adjustment and testing of promoter strengths as described above in Example 1. Increasing the strength of promoter 2, or decreasing the strength of promoter 1, translates the threshold to higher values of x. Parameter values: $\eta=\gamma=2$ for all curves; (FIG. 7A) $\alpha_2=2$ (curve a), $\alpha_2=10$ (curve b), $\alpha_2=20$ (curve c); (FIG. 7B) $\alpha_1=10$ (curve a), $\alpha_1=5$ (curve b), $\alpha_1=3$ (curve c). Increases in $\alpha_2$ (i.e., the strength of promoter 2) move the switching threshold to larger concentrations of activating agent x, but also increase the size of the hysteresis. Reductions in $\alpha_1$, the maximum strength of promoter 1, also move the threshold to higher concentrations of activating agent x and simultaneously reduce the size of the hysteresis. Thus, a switch with the desired threshold and hysteresis characteristics can be designed by choosing promoters of appropriate strengths (i.e., those strengths which produce the desired threshold and hysteresis characteristics). Strengths may be experimentally adjusted according to the qualitative predictions of the theory. Manipulations and assays are the same as those described for the toggle switch construct). Finally, FIG. 7A shows that there are absolute limits to the adjustability of the threshold. For very low values of $\alpha_1$, no switching occurs regardless of the strength of promoter 2. Furthermore, in the experimental system, the promoter strength has a physically determined maximum that will place an upper limit on the location of the switching threshold.

The above discussion shows that, in one embodiment, a sharp rise in transcription of a gene of interest preferably occurs (a) where the first and second repressor proteins form homo-dimers, both $\alpha_1$, and $\alpha_2$ have a value of greater than 2, and (b) where the first and second repressor proteins form homo-multimers other than dimers, either $\alpha_1$, or $\alpha_2$ have a value greater than 1. The minimum permissible value of $\alpha_1$ or of $\alpha_2$ approaches 1 as the degree of multimerization increases, but it does not fall below 1.

Mathematical Analysis of a Multistate Oscillator

An oscillator such as the oscillator shown in FIG. 2A can be modeled by adding a delayed feedback equation to the threshold equations (equations iii, and iv), yielding the following set of equations (v), (vi), and (vii):

$$\frac{d\hat{u}}{d\tau} = \frac{\alpha_1 \hat{x}^\eta}{\hat{x}^\eta + 1 + \hat{v}^\beta} - \hat{u} \quad \text{(v)}$$

$$\frac{d\hat{v}}{d\tau} = \frac{\alpha_2}{1 + \hat{u}^\gamma} - \hat{v} \quad \text{(vi)}$$

$$\frac{d\hat{x}}{d\tau} = \frac{K_d \hat{v} - \hat{x}}{k_d} \quad \text{(vii)}$$

In a more preferred embodiment, adding a delayed feedback yields the following set of equations (v), (vi), and (viii):

$$\frac{d\hat{u}}{d\tau} = \frac{\alpha_1 \hat{x}^\eta}{\hat{x}^\eta + 1 + \hat{v}^\beta} - \hat{u} \quad \text{(v)}$$

$$\frac{d\hat{u}}{d\tau} = \frac{\alpha_2}{1 + \hat{u}^\gamma} - \hat{v} \quad \text{(vi)}$$

-continued $$\frac{d\hat{x}}{d\tau} = \frac{1}{k_d}\left(\frac{K_d \hat{v}^\rho}{1+\hat{v}^\rho} - \hat{x}\right) \quad \text{(viii)}$$

where, $K_d$=strength of promoter 3, $k_d$=time delay which is the time it takes for x to reach ⅔ of its steady-state concentration for a given value of v.

$\rho$=cooperativity of binding of third protein to third promoter.

The other parameters in equations (v) to (viii) are the same as those given in equations (i) to (iv).

FIG. 8 shows the predicted behavior of multi-state oscillator systems of the invention. A simulation of the multi-state oscillator network of FIG. 2A, and modeled by equations (v) and (vi) is shown in FIGS. 8A and 8B. The parameter values are as follows: $\alpha_1\alpha_2=10, k_d=0.6$. A simulation of the multi-state oscillator network of FIG. 2C is shown in FIGS. 8C and 8D. The oscillation period of can be altered by adjusting the time delay, as shown in FIGS. 8A and 8B. The time delay describes the lag in the response of activator (X) relative to proteins u and v. Thus, the time delay can be increased, for example, either by decreasing the rate of degradation of protein X or by increasing the rate of degradation of proteins u and v. Furthermore, the proper tuning of this time delay and the strength of promoter 3 is critical for the production of oscillations. If the delay is too long or too short, or if the promoter is too weak or too strong, the system will not oscillate and, it will settle to a steady-state. These parameters can be manipulated experimentally using methods known in the art to achieve the desired behavior. The time-delay and promoter strength may be adjusted according to the qualitative predictions of the model. Accordingly, based on experimental measurements of the system's behavior, the promoter strength and time delay may be increased or decreased until oscillations are experimentally observed (e.g., through the use of a reporter gene). The strength and time-delay may be altered, for example, by manipulating the DNA sequence of the promoters and the genes. The relative strengths of the promoters that are included in the adjustable-threshold switch portions of the oscillator are preferably as described herein for an adjustable threshold switch.

It is not intended that the repressors, activators, and promoters used in the two-state oscillator constructs of the invention be limited to a particular type or source. Any combination of inducible promoters (and their cognate activators) and constitutive promoters (and their cognate repressors) is suitable for use in the two-state oscillator constructs. Suitable promoters and cognate repressors/ activators are known in the art (e.g., those contained in the Swiss-Prot protein database at http://exasy.hcuge.ch/sprot/sprot-top.html), and include those listed herein and the eukaryotic promoters $P_{hCMV}$, $P_{HSV_{tk}}$, $P_{SV\ 40}$. In addition, artificial eukaryotic activators can be constructed from DNA binding proteins fused with the activation domains such as the Herpes Simplex Virus VP16 activation domain [Gossen & Bujard (1992), supra], the human B42 activation domain [Clontech Laboratories, http://www.clontech.com], or the yeast GAL4 activation domain [Darnell, et al. (1990), supra]. A corresponding cognate inducible promoter is constructed from the DNA recognition sequence of the binding domain fused with a portion of a constitutive eukaryotic promoter.

Furthermore, two-state oscillator constructs provided herein are not intended to be limited to the locations of regulatory gene 1 ($R_1$) in relation to $P_1$ of FIG. 2A, of regulatory gene 2 ($R_2$) and regulatory gene 3 ($R_3$) in relation to $P_2$ of FIG. 2A. Moreover, the invention also includes having one or more genes of interest operably linked to $P_1$-$R_1$ as well as one or more other genes of interest operably linked to $P_2$-$R_2$-$R_3$ of FIG. 2A. The invention also expressly contemplates having one or more genes of interest operably linked to $P_1$-$R_1$-$R_2$ as well as one or more other genes of interest operably linked to $P_2$-$R_3$ of FIG. 2B. Similarly the invention also contemplates having one or more genes of interest operably linked to $P_1$-$R_1$ as well as one or more genes of interest operably linked to $P_2$-$R_2$ of FIG. 2C. Likewise, one or more genes of interest may be linked to $P_3$ in each of the constructs shown in FIGS. 2A, 2B and 2C. Different configurations of the genes and promoters may be used to achieve the desired behavior of the two-state oscillator constructs so long as genes are operably linked to the promoters. Furthermore, it is expressly contemplated that each of the operons of FIG. 2 may be on the same or on different vectors.

Example 3

Construction of an Exemplary Toggle Switch

This Example demonstrates the successful construction and testing of a variety of toggle switches which exhibit bi-stability and an ideal switching threshold.

All the toggle switches described herein were constructed using *E. coli* plasmids conferring ampicillin resistance and containing the pBR322 ColEl replication origin. Each toggle switch comprised two repressors and two constitutive promoters wherein each promoter was inhibited by the repressor transcribed by the opposing promoter. The toggle switch genes were arranged as a Type IV plasmid as shown in FIG. 9D. In FIG. 9D, the promoters are denoted by solid rectangles with arrowheads, genes are denoted with solid rectangles, ribosome binding sites and terminators ($T_1$, $T_2$) are denoted by outlined boxes. The Ptrc-2 promoter ($P_2$) with RBS-E (RBS2) and the lacI gene ($R_1$) were used in all Type II, III and IV plasmids (FIGS. 9B, 9C and 9D, respectively). RBS-B (shown in FIG. 10) was used for the reporter gene in all Type IV plasmids. Different $P_1$ promoters, RBS1 ribosome binding sites, and/or $R_2$ repressors, were used for the various toggle switches. The two opposing promoters and repressor genes were arranged back-to-back in opposite orientation to minimize unintended phenomena such as transcription read-through and antisense transcription. Though all genes were contained on a single plasmid, the two halves of the toggle can, in principle, be placed on separate plasmids without altering the functionality of the toggle.

i. Plasmid Construction

Two classes of toggle switches were constructed—the pTAK class (Class 1) and the pIKE class (Class 2). Both classes contained the Lac repressor (lacI) in conjunction with the Ptrc-2 promoter for the first promoter-repressor pair. For the second promoter-repressor pair, the pTAK plasmids (Class 1) contained the $P_L$s1con promoter in conjunction with a temperature-sensitive mutant of the λ repressor (cIts). The pTAK plasmids were switched between states by a pulse of IPTG or by a thermal pulse. For the second promoter-repressor pair, the pIKE plasmids (Class 2) contained the $P_L$tetO-1 constitutive promoter in conjunction with the TetR repressor (tet R). The pIKE plasmids were switched between states by a pulse of IPTG or a pulse of anhydrotetracycline (aTc). In total, four variants of the pTAK based toggles and two variants of the pIKE based toggles were constructed and tested herein.

Plasmids were constructed using basic molecular cloning techniques described in standard cloning manuals [Ausubel et al. in *Current Protocols in Molecular Biology* (Wiley, New York, 1987); Sambrook et al. in *Molecular Cloning: A Laboratory Manual* (Cold Spring Harbor Laboratory Press, Plainview, N.Y., 1989)]. Restriction enzymes were purchased from New England Biolabs and Promega; PfuTurbo polymerase was purchased from Stratagene; all other enzymes were purchased from New England Biolabs; all synthetic oligonucleotides were purchased from Operon Technologies. All genes, promoters and transcription terminators were obtained by PCR amplification using PfuTurbo proofreading polymerase and synthetic primers with overhanging ends containing the appropriate restriction sites. Ribosome binding sites were included in the overhanging ends of the primers. Site mutations were performed using either the Stratagene QuickChange or ExSite protocols in accordance with the manufacturers instructions.

Genes, promoters and transcription terminators were obtained as follows: Ptrc-2 from pTrc99a (AP Biotech), $P_L$ from pXC46 (ATCC), $P_L$tetO-1 by total synthesis according to the published sequence [Lutz & Bujard (1997) Nucleic Acids Res. 25:1203–1210], lacI from pTrc99a, cIts from pGW7 (ATCC), tetR from pcDNA6/TR (Invitrogen), gpfuv from pGFPuv (Clontech), gfpmut3 from pJBAIII (gift of J. B. Andersen, Technical University of Denmark), and rrnT1T2 terminators from pTrc99a. All plasmids contained the ampicillin resistance region and ColEl origin of replication from the pTrc99a plasmid. All cloning was performed by TSS transformation [Ausubel et al. in *Current Protocols in Molecular Biology* (Wiley, New York, 1987)] into either *E. coli* strain JM2.300 (CGSC), JC158 (CGSC), or TAP106 (ATCC). DNA sequencing was performed using a Perkin-Elmer ABI Prism 377 Sequencer.

In all toggle plasmids, the gfpmut3 reporter gene was arranged as the second cistron downstream of the Ptrc-2 promoter. Thus, transcription from Ptrc-2 (and repression of $P_1$) results in the expression of GFPmut3. For clarity, this state is termed the "high" state. The opposing state, in which $P_1$ is transcribed and Ptrc-2 is repressed, is termed the "low" state. Unless otherwise indicated, GFPmut3 is the reporter used in all plasmids. Gfpmut3, a mutant of wild-type GFP containing S65G and S72A substitutions, is optimized for flow cytometry [Cormack et al. (1996) Gene 173:33–38]. This mutant is approximately 50–70 times brighter than GFPuv when expressed in *E. coli* and assayed in a FACS-Calibur flow cytometer.

Figure 10A:
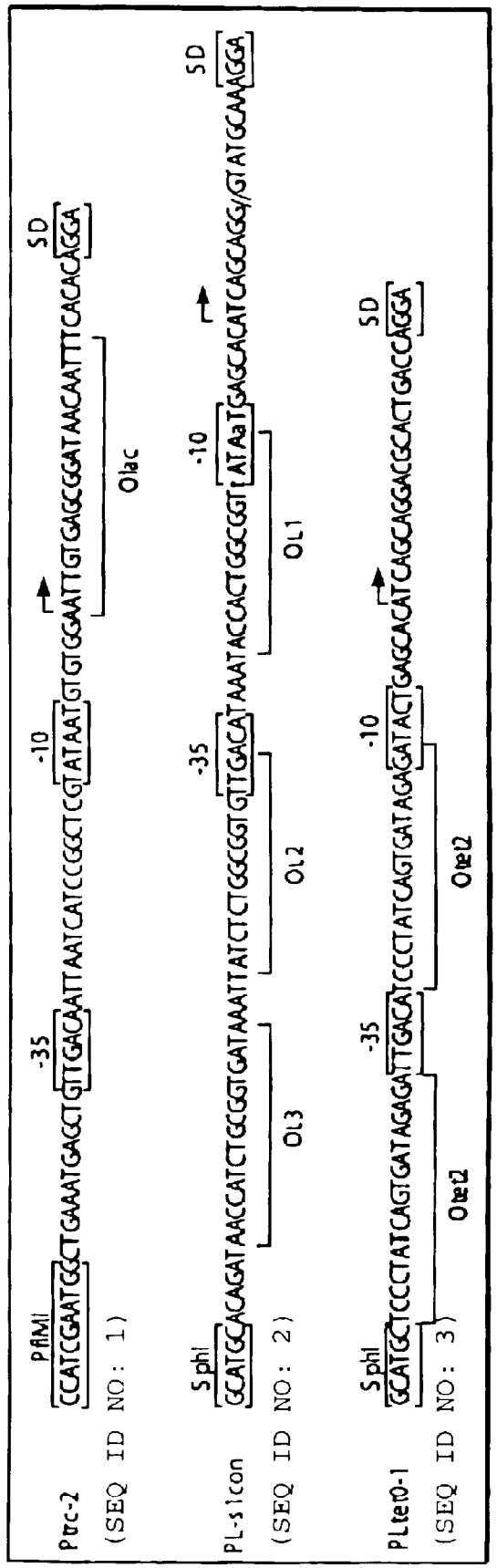
FIG. 10 shows the nucleic acid sequence of promoters (FIG. 10A) and ribosome binding sites (FIG. 10B) used to construct toggle switch plasmids.

The promoters used in the toggle were $P_L$tetO-1 (TetR repressed), Ptrc-2 (LacI repressed) and $P_L$s1con (CI repressed). The ranked order of the transcriptional efficiencies of the promoters is $P_L$s1con>Ptrc-2>$P_L$tetO-1. In all variants of the toggle switch, the sequence of the three promoters was unchanged. The rates of synthesis of the repressors ($\alpha_1$ and $\alpha 2$ in the model) or the reporter genes are modified by exchanging the downstream ribosome binding sites (RBS). The structures of the three promoters and the various ribosome binding sites used in the toggle switches are illustrated in FIGS. 10A and 10B, respectively (SEQ ID NOS: 1–11). In FIG. 10A, the upstream limit of each promoter is marked by the indicated restriction site. Operator sites are marked by a single underbracket. The initiation of transcription is denoted with arrows. SD denotes the Shine-Dalgarno sequence. Mutations in the −10 sequence of $P_L$s1con are indicated with lowercase letters. In FIG. 10B, the Shine-Dalgarno sequences "AGGA" and start codons "ATG" are presented. The various sequences are ranked in order of their translational efficiency (A being the highest, H being the lowest)

Bases −48 to +27 of the Ptrc promoter, where +1 is the initiation of transcription, were amplified by PCR from pTrc99a to form the Ptrc-2 promoter. Ptrc-2 is a highly efficient fusion of the Ptrp and Plac promoters and is nearly identical to the commonly used Ptac promoter. $P_L$s1con is a shortened version of the wild-type $P_L$ promoter with additional mutations conferring a consensus −10 sequence. $P_L$s1con was amplified from bases −75 to the Shine-Dalgarno sequence of pXC46. Thus $P_L$s1con eliminates the $P_{L2}$ secondary promoter and the $L_1$ and L2 integration host factor binding sites of the wild-type $P_L$ promoter [Giladi et al. (1992) J. Mol. Biol. 224:937–948]. Elimination of $P_{L2}$, L1, L2 and introduction of the −10 mutations serve to weaken the native strength of the extremely strong $P_L$ promoter while retaining all three operators for λ repressor binding. The $P_L$tetO-1 promoter, obtained through total synthesis according to the published sequence [Lutz & Bujard (1997) Nucleic Acids Res. 25:1203–1210], contains two copies of the $O_2$ operator of the TnlO tetracycline resistance operon—one between the consensus −35 sequence and the −10 sequence of $P_L$, and one upstream of the −35 sequence. The $P_L$tetO-1 promoter was substantially less efficient than both Ptrc-2 and $P_L$s1con, but it was effectively repressed by the wild-type TetR repressor.

ii. Strains, Growth Conditions, Chemicals

The host cell for all promoter assays and toggle switch experiments was *E. coli* strain JM2.300 [λ-, lacI22, rpsLl35 (StrR), thi-1] (CGSC strain 5002). JM2.300, which contains few mutations and is a fast growing strain that can tolerate enormous overexpression of plasmid-bound genes. Because JM2.300 contains no λ repressor and carries a non-functional Lac repressor (lacI22), it is considered to be a suitable host for the toggle switch.

All cells were grown in LB medium (Difco) with 100 μg/ml ampicillin plus inducers as indicated in the text. All Type I and pIKE series plasmids were grown at 37±1° C., unless otherwise indicated. All pTAK series plasmids were grown at 32±1° C. except during thermal induction. Thermal induction was carried out at 42±1° C., unless otherwise indicated. For all expression tests, cells were maintained in logarithmic growth phase by periodic 500–1000 fold dilution into fresh medium.

Ampicillin and IPTG were purchased from Sigma. Anhydrotetracycline was purchased from ACROS Organics. All other chemicals were obtained from Fisher.

iii. Assay of Gene Expression And Promoter Strength

The following expression data was collected using a Becton-Dickinson FACSCalibur flow cytometer with a 488 nm argon excitation laser and a 515–545 nm emission filter. Prior to each assay, cells were pelleted and resuspended in 0.22 μm filtered phosphate buffered saline (58 mM $Na_2HPO_4$, 17 mM $NaH_2PO_4$, 68 mM NaCl, pH=7.4). Cells were assayed at low flow rate and fluorescence was calibrated using InSpeck Green fluorescent beads (Molecular Probes). All measurements of gene expression were obtained from three independent cultures maintained simultaneously under identical conditions. For each culture, 40,000 events were collected. All flow data were converted to ASCII format using MFI (E. Martz, University of Massachusetts, Amherst, available at http://marlin.bio.umass.edu/mcbfacs/flowcat.html\##mfi) and analyzed with Matlab (Mathworks).

The strengths, in calibrated fluorescence units, of the promoter/RBS pairs used to construct the toggle switches are listed in Table 4. Measurements of promoter strengths were performed using Type I plasmids (FIG. 9A) and assays were performed as described above. Leakage expression from the promoters under fully repressed conditions is also listed in Table 4.

The efficacy of repression was tested using Type II plasmids (for LacI repression) (FIG. 9B) or Type III plasmids (for cI or TetR repression) (FIG. 9C). The efficiency of the three repressors, as used in the toggle switches can be estimated by comparing the strength of the bare promoters in Type I plasmids against their leakage expression under repressed conditions. For example, the extremely efficient λ repressor (cI), expressed from Ptrc-2-E, achieves ~6000 fold (14,300/2.5) repression of the $P_L$s1con-D promoter (Table 4). On the other hand, the TetR repressor, also expressed from Ptrc-2-E, achieves only ~100 fold (660/5.8) repression of the $P_L$tetO-1-A promoter (Table 4).

TABLE 4

Gene Expression by Plasmids

| PLASMID | TYPE | P1 | RBS1 | RBS2 | GFP EXPRESSION |
|---|---|---|---|---|---|
| Bare Promoters | | | | | |
| pMKN7a* | I | Ptrc-2 | E | — | 732 ± 108 |
| pBAG102 | I | $P_L$tetO-1 | C | — | 5.5 ± 0.1 |
| pBAG103 | I | $P_L$tetO-I | A | — | 660 ± 42 |
| pBRT21.1* | I | $P_L$s1con | D | — | 9,390 ± 840 |
| pBRT21.1*† | I | $P_L$s1con | D | — | 14,300 ± 400 |
| pBRT123 | I | $P_L$s1con | G | — | 387 ± 21 |
| pBRT124 | I | $P_L$s1con | F | — | 972 ± 43 |
| pBRT125 | I | $P_L$s1con | H | — | 15.9 ± 3.2 |
| LacI Repression | | | | | |
| pTAK102 | II | $P_L$s1con | D | — | 36.0 ± 3.8 |
| pTAK103a | II | $P_L$s1con | G | — | 137 ± 8 |
| cI Repression | | | | | |
| pTAK106 | III | $P_L$s1con | D | — | 2.5 ± 0.3 |
| pTAK107 | III | $P_L$s1con | G | — | 2.0 ± 0.1 |
| TetR Repression | | | | | |
| pIKE108 | III | $P_L$tetO-1 | A | — | 5.8 ± 1.0 |
| pIKE110 | III | $P_L$tetO-1 | C | — | 2.3 ± 0.2 |
| Toggles | | | | | |
| pTAK117 | IV | $P_L$s1con | D | B | Bistable |
| pTAK130 | IV | $P_L$s1con | G | B | Bistable |
| pTAK131 | IV | $P_L$s1con | F | B | Bistable |
| pTAK132 | IV | $P_L$s1con | H | B | Bistable |
| pIKE105 | IV | $P_L$tetO-1 | A | B | Monostable |
| pIKE107 | IV | $P_L$tetO-1 | C | B | Bistable |

*Estimated from flow-cytometer assay of GFPuv-expressing promoters.
†Grown at 32° C.

iv. Demonstration of Bi-Stability

In order to test the limits of bistability of the toggle switch, the $\alpha_1$ parameter was varied experimentally by inserting RBS1 sequences of varying efficiency into Class 1 and Class 2 toggle switches of Type IV. Four pTAK series plasmids (Class 1) were constructed with RBS1 sequences D, F, G and H, and two pIKE series plasmids (Class 2) were constructed with RBS1 sequences A and C (Table 4). All four pTAK plasmids exhibited bistability, while only one pIKE plasmid (pIKE107) exhibited bistability.

Figure 11A:
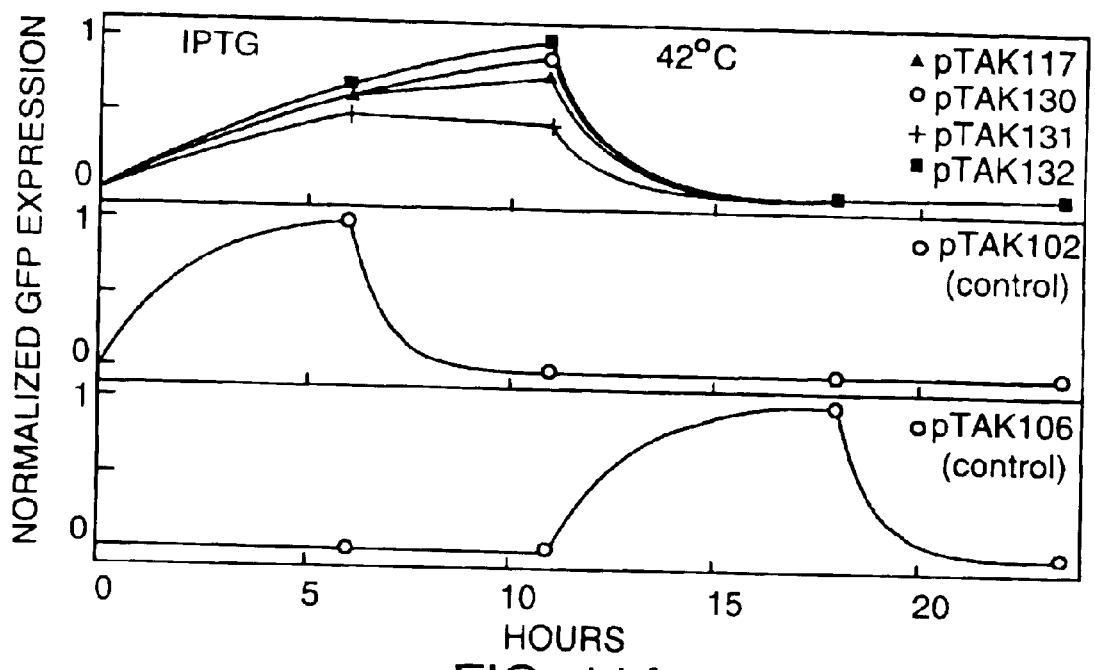
FIGS. 11A–11C are graphs demonstrating bistability of exemplary toggle switches: Class 1 toggles and controls (FIG. 11A); Class 2 toggles and controls (FIG. 11B); long-term test of pTAKI17 bistability (FIG. 11C).
Figure 11B:
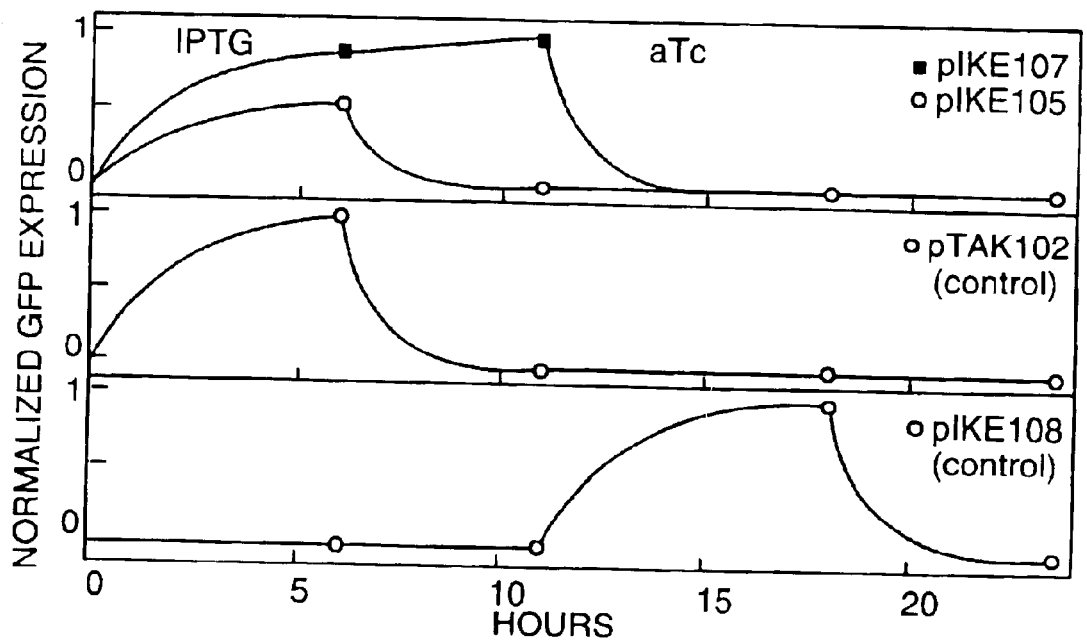

The existence of bistability is illustrated in FIG. 11. In this experiment, the toggle and control plasmids were grown in E. coli strain JM2.300 for 23.5 hours. At 6, 11, 18 and 23.5 hours, samples were taken and cells were pelleted, washed once in LB or PBS, and diluted 500–1000 fold into fresh medium with or without inducers as appropriate. Cells were initially grown for 6 hours with 2 mM IPTG, inducing GFPmut3 expression in all toggles and the IPTG-inducible pTAK102 control plasmid (FIGS. 11A and 11B). The thermally-inducible pTAK106 control (FIG. 11A) and the aTc-inducible pIKE108 control (FIG. 11B) did not express GFPmut3 in the presence of IPTG. Cells were washed and diluted into fresh medium with no IPTG and grown an additional 5 hours. The five bistable toggle plasmids, which had been switched to the high state by the IPTG pulse, continued to express GFPmut3 in the absence of inducer, while the pTAK102 control plasmid and the monostable pIKE105 toggle plasmid, returned to the low state (FIGS. 11A and 11B). Cells were diluted into fresh medium and induced at 42° C. (pTAK plasmids only—FIG. 11A) or grown in the presence of 500 ng/ml aTc (pIKE plasmids only—FIG. 11B). After 7 hours growth, GFPmut3 expression in all toggles had been shut off, while GFPmut3 expression in the thermally-inducible pTAK106 control and the aTc-inducible pIKE108 control was up-regulated. Cells were washed and diluted into fresh medium with no inducers or returned to standard temperature. After an additional 5.5 hours, the five bistable toggle plasmids, which had been switched to the low state, continued to repress GFPmut3 expression, while the pTAK106 and pIKE108 controls returned, as expected, to their non-induced condition.

Figure 11C:
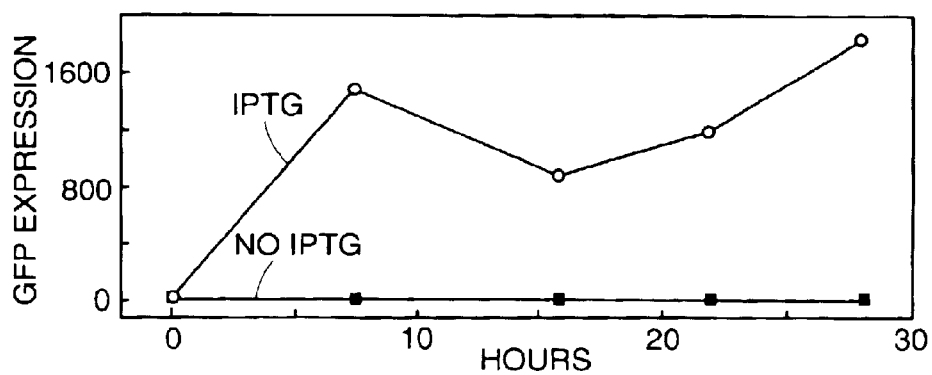

FIG. 11C shows the long-term stability of the two states of the pTAK117 toggle switch. In this experiment, a single culture of pTAK117 cells (initially in the low state) was divided into two groups and diluted. The first group was grown in medium with no inducers (squares) while the second group was grown in medium plus 2mM IPTG (circles). After 6 hours, cells were pelleted, washed once in LB and diluted 1000 fold into fresh medium with no inducer. Both groups of cells were grown for an additional 22 hours while taking samples and diluting into fresh medium every 6–8.5 hours. The two groups of pTAK117 cells remained in their initial high or low states for the entire 22 hour period.

Although all of the toggle plasmids contained the same configuration of elements, one plasmid, pIKE105, did not exhibit bistability. This result probably is due to the reduced efficiency of the TetR repressor relative to the λ repressor. To maintain bistability, the reduced efficiency requires a corresponding decrease in the strength of the $P_L$tetO-1 promoter relative to the $P_L$S1con promoter. The $P_L$tetO-1 in the pIKE105 plasmid apparently is not sufficiently reduced in strength to achieve bistability. However, the strength reduction provided by the $P_L$tetO-1 promoter in the pIKE107 plasmid is sufficient.

Example 4

Figure 12A:
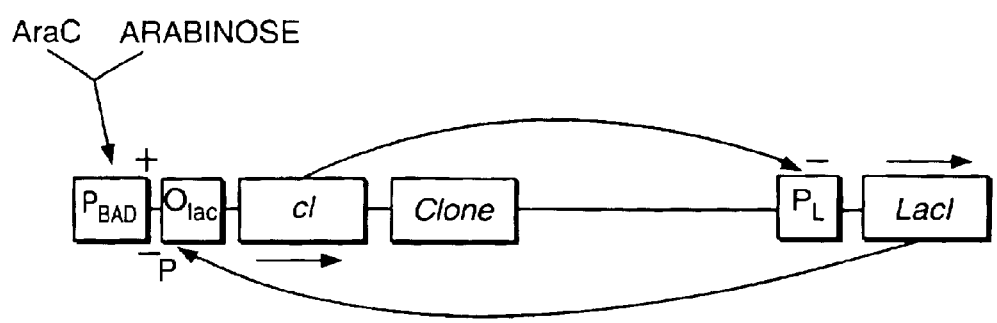
FIG. 12 provides illustrations of an exemplary eukaryotic adjustable-threshold toggle (FIG. 12A) and nucleic acid sequences of the $P_{bad}$ promoter fused to the $O_{lac}$ operator region of the $P_{trc}$ promoter (FIG. 12B).

Design and Construction of a Plasmid Carrying an Exemplary Adjustable-Threshold Switch The experimental methods used to construct and test adjustable-threshold switch constructs are similar to those discussed for the toggle switch constructs described in U.S. Ser. No. 09/872,868. It is contemplated that elements of an adjustable-threshold switch construct may be arranged in the same configuration as those in the toggle switch construct except that one of the constitutive promoters is replaced by a promoter that is activatable by an activating agent (see, FIG. 12A). Additionally, expression from this promoter preferably is negligible in the absence of the activating agent. Finally, this promoter preferably is simultaneously suppressed by the opposing gene in the switch construct (i.e., regulatory gene 2 in FIG. 1. Construction of a promoter that satisfies all of the above requirements is facilitated by the modular structure of the $P_{trc}$ promoter used in Example 3. The Lac repressor binding site begins at the first nucleotide of the mRNA transcript. The complete $P_{trc}$ promoter, including all of the RNAP recognition sites, is located upstream of the Lac repressor binding site. Thus, the entire $P_{trc}$ promoter upstream of the +1 nucleotide may be removed and replaced by nearly any positively regulated promoter element, such as the promoters set forth in Table 2. The new hybrid promoter, which retains the Lac repressor binding site, is thus both positively and negatively regulated. For example, the Pbad promoter, which is activated by the AraC protein in the presence of arabinose, is fused to the $O_{lac}$ operator region of $P_{trc}$ (FIG. 12B, SEQ ID NO: 12). The resulting hybrid promoter is positively activated by AraC-arabinose and repressed by lacI (FIG. 12A).

The opposing promoter may remain unaltered, or its strength may be modified in order to adjust the threshold location or hysteresis. Such strength modifications may also be necessary for the hybrid activator/repressor promoter. The modifications can be introduced through standard recombinant DNA techniques.

Dynamic adjustment of the threshold concentration of the inducing agent exemplified by activating agent in FIG. 1 is also possible. Because the strengths of the promoters ($\alpha_1$ and $\alpha_2$) are dependent on the strength of repressor-DNA binding, an inducer compound such as IPTG can be used to alter the promoter strength. The inducer, by competitively binding the repressor, effectively raises the dissociation constant of the repressor-DNA binding. Thus, by adjusting the concentration of inducer in the medium, the threshold can be dynamically altered.

Many suitable activatable promoters are known in the art. These and their cognate activators are exemplified by the activators/promoters discussed herein.

Example 5

Design and Construction of Plasmids Carrying a Two-State Oscillator

Methods used to construct and test two-state oscillators are similar to those outlined for a bistable toggle switch construct described in U.S. Ser. No. 09/872,868. The design of a two-state oscillator is an extension of the adjustable-threshold switch as discussed above. The output of the adjustable-threshold switch (i.e., the expression of one of the two genes) is fed back into the input of the switch (e.g., via an activator protein concentration), preferably with a time delay. There are two general methods to achieve this feedback.

The first general method, illustrated in FIG. 2A, is to place the expression of the activator (e.g., protein $R_4$) under the indirect control of $P_2$. The increase in concentration of $R_3$ under the control of $R_2$ is necessary to produce the required delay. Thus, promoter 2 directs the transcription of two genes, the product of one gene represses promoter 1 and the product of the other gene activates promoter 3.

In the second general method, illustrated in FIGS. 2B and 2C, $P_3$ is also a constitutive promoter that is repressed by a product of $P_1$.

For both the first and second methods, activators and repressors which are suitable for the feedback genes are known in the art and described herein. Modification of these elements is likely to be necessary to achieve the desired time delay. For example, the time delay can be increased either by decreasing the rate of degradation of the activator protein or by increasing the rate of degradation of the proteins encoded by regulatory genes 1, 2 and 3 ($R_1$, $R_2$ and $R_3$) in the gene networks shown in FIG. 2A and 2B, or by regulatory genes 1 and 2 ($R_1$ and $R_2$) in the gene network shown in FIG. 2C.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

Incorporation by Reference

Each of the patent documents and scientific publications disclosed herein is incorporated by reference into this application in its entirety.

What is claimed is:

1. A recombinant multi-state genetic oscillator comprising:
   (a) a first nucleic acid construct comprising a first inducible promoter operably associated with a first gene encoding a first protein;
   (b) a second nucleic acid construct comprising a promoter operably associated with a second gene encoding a second protein and to a third gene encoding a third protein, wherein transcription from the promoter is active in the absence of a repressor; and
   (c) a third nucleic acid construct comprising a second inducible promoter operably associated with a fourth gene encoding a fourth protein, wherein
      (i) the first protein, when produced, is capable of repressing transcription from the promoter of part (b),
      (ii) the second protein, when produced, is capable of repressing transcription from the first inducible promoter,
      (iii) the third protein, when produced, is capable of increasing transcription from the second inducible promoter, and
      (iv) the fourth protein, when produced, is capable of increasing transcription from the first inducible promoter.

2. The genetic oscillator of claim 1, wherein the first and second proteins are DNA binding proteins capable of repressing transcription from the promoter of part (b).

3. The genetic oscillator of claim 1, wherein the first inducible promoter, the promoter of part (b) or the second inducible promoter is operably associated with an operator.

4. The genetic oscillator of claim 1, wherein the third and fourth proteins are DNA binding proteins capable of increasing transcription from an inducible promoter.

5. The genetic oscillator of claim 1, wherein the first construct further comprises a gene of interest in operable association with the first inducible promoter.

6. The genetic oscillator of claim 5, wherein expression of the gene of interest increases and decreases periodically.

7. The genetic oscillator of claim 1, wherein the second nucleic acid construct further comprises a gene of interest in operable association with the promoter of part (b).

8. The genetic oscillator of claim 7, wherein expression of the gene of interest increases and decreases periodically.

9. The genetic oscillator of claim 1, wherein the first and second nucleic acid constructs are comprised within a single contiguous nucleic acid molecule.

10. An isolated host cell comprising the genetic oscillator of claim 1.

11. The isolated host cell of claim 10, wherein the host cell is a prokaryotic cell.

12. The isolated host cell of claim 10, wherein the host cell is a eukaryotic cell.

13. The isolated host cell of claim 10, wherein the host cell is a cell in culture.

* * * * *

SEQUENCE LISTING

```
<160> NUMBER OF SEQ ID NOS: 12

<210> SEQ ID NO 1
<211> LENGTH: 90
<212> TYPE: DNA
<213> ORGANISM: Artificial Sequence
<220> FEATURE:
<223> OTHER INFORMATION: Promoter Ptrc-2

<400> SEQUENCE: 1
ccatcgaatg gctgaaatga gctgttgaca attaatcatc cggctcgtat aatgtgtgga      60
attgtgagcg gataacaatt tcacacagga                                      90

<210> SEQ ID NO 2
<211> LENGTH: 102
<212> TYPE: DNA
<213> ORGANISM: Artificial Sequence
<220> FEATURE:
<223> OTHER INFORMATION: Promoter PL-slcon

<400> SEQUENCE: 2
gcatgcacag ataaccatct gcggtgataa attatctctg gcggtgttga cataaatacc      60
actggcggtt ataatgagca catcagcagg gtatgcaaag ga                        102
```

<210> SEQ ID NO 3
<211> LENGTH: 84
<212> TYPE: DNA
<213> ORGANISM: Artificial Sequence
<220> FEATURE:
<223> OTHER INFORMATION: Promoter Pltet0-1

<400> SEQUENCE: 3
gcatgctccc tatcagtgat agagattgac atccctatca gtgatagaga tactgagcac    60
atcagcagga cgcactgacc agga    84

<210> SEQ ID NO 4
<211> LENGTH: 15
<212> TYPE: DNA
<213> ORGANISM: Artificial Sequence
<220> FEATURE:
<223> OTHER INFORMATION: Ribosome Binding Site A

<400> SEQUENCE: 4
aggaggaaaa aaatg    15

<210> SEQ ID NO 5
<211> LENGTH: 13
<212> TYPE: DNA
<213> ORGANISM: Artificial Sequence
<220> FEATURE:
<223> OTHER INFORMATION: Ribosome Binding Site B

<400> SEQUENCE: 5
aggaatttaa atg    13

<210> SEQ ID NO 6
<211> LENGTH: 15
<212> TYPE: DNA
<213> ORGANISM: Artificial Sequence
<220> FEATURE:
<223> OTHER INFORMATION: Ribosome Binding Site C

<400> SEQUENCE: 6
aggaaacaga ccatg    15

<210> SEQ ID NO 7
<211> LENGTH: 17
<212> TYPE: DNA
<213> ORGANISM: Artificial Sequence
<220> FEATURE:
<223> OTHER INFORMATION: Ribosome Binding Site D

<400> SEQUENCE: 7
aggaaaccgg ttcgatg    17

<210> SEQ ID NO 8
<211> LENGTH: 15
<212> TYPE: DNA
<213> ORGANISM: Artificial Sequence
<220> FEATURE:
<223> OTHER INFORMATION: Ribosome Binding Site E

<400> SEQUENCE: 8
aggaaaccgg ttatg    15

<210> SEQ ID NO 9
<211> LENGTH: 14
<212> TYPE: DNA

```
<213> ORGANISM: Artificial Sequence
<220> FEATURE:
<223> OTHER INFORMATION: Ribosome Binding Site F

<400> SEQUENCE: 9
aggacggttc gatg                                                              14

<210> SEQ ID NO 10
<211> LENGTH: 16
<212> TYPE: DNA
<213> ORGANISM: Artificial Sequence
<220> FEATURE:
<223> OTHER INFORMATION: Ribosome Binding Site G

<400> SEQUENCE: 10
aggaaaggcc tcgatg                                                            16

<210> SEQ ID NO 11
<211> LENGTH: 14
<212> TYPE: DNA
<213> ORGANISM: Artificial Sequence
<220> FEATURE:
<223> OTHER INFORMATION: Ribosome Binding Site H

<400> SEQUENCE: 11
aggacggccg gatg                                                              14

<210> SEQ ID NO 12
<211> LENGTH: 146
<212> TYPE: DNA
<213> ORGANISM: Artificial Sequence
<220> FEATURE:
<223> OTHER INFORMATION: Pbad promoter fused to the Olac operator region
      of the Ptrc promo te

<400> SEQUENCE: 12
gcgtcacact ttgctatgcc atagcatttt tatccataag attagcggat cctacctgac            60
gctttttatc gcaactctct actgtttctc catagatcta atgtgtggaa ttgtgagcgg           120
ataacaattt cacacaggaa accggt                                                146
```